US011782049B2

(12) United States Patent
Purves

(10) Patent No.: US 11,782,049 B2
(45) Date of Patent: Oct. 10, 2023

(54) APPARATUS AND METHOD FOR COLLECTING A BREATH SAMPLE USING A CONTAINER WITH CONTROLLABLE VOLUME

(71) Applicant: Picomole Inc., Moncton (CA)

(72) Inventor: Christopher Quentin Purves, Moncton (CA)

(73) Assignee: PICOMOLE INC., Moncton (CA)

( * ) Notice: Subject to any disclaimer, the term of this patent is extended or adjusted under 35 U.S.C. 154(b) by 502 days.

(21) Appl. No.: 16/805,142

(22) Filed: Feb. 28, 2020

(65) Prior Publication Data

US 2021/0267478 A1 Sep. 2, 2021

(51) Int. Cl.
| | |
|---|---|
| *G01N 33/497* | (2006.01) |
| *A61B 5/087* | (2006.01) |
| *A61B 5/093* | (2006.01) |
| *G01N 33/00* | (2006.01) |
| *G01N 33/50* | (2006.01) |
| *A61B 10/00* | (2006.01) |

(52) U.S. Cl.
CPC .......... *G01N 33/497* (2013.01); *A61B 5/087* (2013.01); *A61B 5/093* (2013.01); *G01N 33/0009* (2013.01); *G01N 33/5008* (2013.01); *A61B 2010/0087* (2013.01); *G01N 2033/4975* (2013.01)

(58) Field of Classification Search
CPC ............. G01N 33/0009; G01N 33/497; G01N 33/5008; G01N 2033/4975; A61B 5/087; A61B 5/093; A61B 2010/0087
See application file for complete search history.

(56) References Cited

U.S. PATENT DOCUMENTS

| | | | |
|---|---|---|---|
| 3,517,330 | A | 6/1970 | Doyle et al. |
| 4,410,271 | A | 10/1983 | Matthews |
| 4,468,773 | A | 8/1984 | Seaton |
| 4,648,714 | A | 3/1987 | Benner et al. |
| 4,672,618 | A | 6/1987 | Wijntjes et al. |
| 4,779,279 | A | 10/1988 | Brown |

(Continued)

FOREIGN PATENT DOCUMENTS

| | | |
|---|---|---|
| CA | 2792032 A1 | 9/2011 |
| CA | 2997070 A1 | 9/2019 |

(Continued)

OTHER PUBLICATIONS

Orr et al. "Cavity ringdown spectroscopy with widely tunable swept-frequency lasers," European Quantum Eletronics Conference, 2005 *EQEC '05) Jun. 12-17, 2005, p. 204.

(Continued)

*Primary Examiner* — Benjamin R Schmitt
(74) *Attorney, Agent, or Firm* — Ridout & Maybee LLP

(57) ABSTRACT

An apparatus and method for collecting a breath sample are provided. The apparatus has a breath input interface configured to receive exhaled breath, a container connected to the breath input interface for receiving at least some of the exhaled breath, the container having a cavity with a volume that is controllable, and at least one controller configured to control the volume of the cavity to increase at a volume increase rate that is at most equal to a flow rate of the exhaled breath received by the breath input interface.

21 Claims, 16 Drawing Sheets

(56) References Cited

U.S. PATENT DOCUMENTS

| | | | |
|---|---|---|---|
| 4,784,486 | A | 11/1988 | Van Wagenen et al. |
| 4,964,132 | A | 10/1990 | Fischer |
| 5,014,278 | A | 5/1991 | Deki |
| 5,029,174 | A | 7/1991 | Anderson et al. |
| 5,091,912 | A | 2/1992 | Bretenaker et al. |
| 5,135,304 | A | 8/1992 | Miles et al. |
| 5,465,728 | A | 11/1995 | Phillips |
| 5,528,040 | A | 6/1996 | Lehmann |
| 5,573,005 | A | 11/1996 | Ueda et al. |
| 5,646,952 | A | 7/1997 | Whittley |
| 5,815,277 | A | 9/1998 | Zare et al. |
| 5,903,358 | A | 5/1999 | Zare et al. |
| 5,912,740 | A | 6/1999 | Zare et al. |
| 6,076,392 | A | 6/2000 | Drzewiecki |
| 6,084,682 | A | 7/2000 | Zare et al. |
| 6,233,052 | B1 | 5/2001 | Zare et al. |
| 6,324,191 | B1 | 11/2001 | Horvath |
| 6,363,772 | B1 | 4/2002 | Berry |
| 6,466,322 | B1 | 10/2002 | Paldus et al. |
| 6,479,019 | B1 | 11/2002 | Goldstein et al. |
| 6,504,145 | B1 | 1/2003 | Romanini et al. |
| 6,540,691 | B1 | 4/2003 | Phillips |
| 6,563,583 | B2 | 5/2003 | Ortyn et al. |
| 6,582,376 | B2 | 6/2003 | Baghdassarian |
| 6,726,637 | B2 | 4/2004 | Phillips |
| 6,727,492 | B1 | 4/2004 | Ye et al. |
| 6,865,198 | B2 | 3/2005 | Taubman |
| 6,952,945 | B2 | 10/2005 | O'Brien |
| 7,004,909 | B1 | 2/2006 | Patel et al. |
| 7,012,696 | B2 | 3/2006 | Orr et al. |
| 7,101,340 | B1 | 9/2006 | Braun |
| 7,106,763 | B2 | 9/2006 | Tan et al. |
| 7,235,054 | B2 | 6/2007 | Eckerbom |
| 7,352,463 | B2 | 4/2008 | Bounaix |
| 7,391,517 | B2 | 6/2008 | Trebbia et al. |
| 7,450,240 | B2 | 11/2008 | Morville et al. |
| 7,541,586 | B2 | 6/2009 | Miller |
| 7,555,024 | B2 | 6/2009 | Ishaaya et al. |
| 7,569,823 | B2 | 8/2009 | Miller |
| 7,606,274 | B2 | 10/2009 | Mirov et al. |
| 7,612,885 | B2 | 11/2009 | Cole et al. |
| 7,613,216 | B2 | 11/2009 | Nakagawa |
| 7,616,123 | B2 | 11/2009 | Ridder et al. |
| 7,646,485 | B2 | 1/2010 | Tan |
| 7,679,750 | B2 | 3/2010 | Li et al. |
| 7,902,534 | B2 | 3/2011 | Cole et al. |
| 8,018,981 | B2 | 9/2011 | Eckles et al. |
| 8,288,727 | B2 | 10/2012 | Cormier et al. |
| 8,659,758 | B2 | 2/2014 | Koulikov et al. |
| 8,659,759 | B2 | 2/2014 | Koulikov et al. |
| 8,665,442 | B2 | 3/2014 | Koulikov et al. |
| 8,885,167 | B2 | 11/2014 | Koulikov et al. |
| 8,982,352 | B1 | 3/2015 | Hoffnagle et al. |
| 9,014,221 | B2 | 4/2015 | Kub et al. |
| 9,097,583 | B2 | 8/2015 | Gupta et al. |
| 9,194,742 | B2 | 11/2015 | Kachanov et al. |
| 9,212,990 | B1 | 12/2015 | Muraviev |
| 9,568,465 | B2 | 2/2017 | Rihani et al. |
| 9,625,702 | B2 | 4/2017 | Hodges et al. |
| 9,671,332 | B2 | 6/2017 | Christensen |
| 9,778,110 | B1 | 10/2017 | Rella et al. |
| 9,918,661 | B2 | 3/2018 | Cormier et al. |
| 10,034,621 | B2 | 7/2018 | Wondka et al. |
| 10,130,284 | B2 | 11/2018 | Johnson |
| 10,139,392 | B2 | 11/2018 | Kaariainen et al. |
| 10,168,275 | B2 | 1/2019 | Orcutt |
| 10,194,833 | B2 | 2/2019 | Cormier |
| 10,234,381 | B2 | 3/2019 | Koulikov |
| 10,330,592 | B2 | 6/2019 | Koulikov |
| 10,401,281 | B2 | 9/2019 | Koulikov |
| 10,499,819 | B2 | 12/2019 | Wondka et al. |
| 10,527,492 | B2 | 1/2020 | Bouzid |
| 2003/0109794 | A1 | 6/2003 | Phillips |
| 2004/0022281 | A1 | 2/2004 | Steffens et al. |
| 2004/0137637 | A1 | 7/2004 | Wang et al. |
| 2004/0142484 | A1 | 7/2004 | Berlin et al. |
| 2004/0162500 | A1 | 8/2004 | Kline |
| 2004/0190563 | A1 | 9/2004 | Gendron |
| 2005/0134836 | A1 | 6/2005 | Paldus et al. |
| 2005/0177056 | A1 | 8/2005 | Giron et al. |
| 2005/0177057 | A1 | 8/2005 | Friedman et al. |
| 2005/0201428 | A1 | 9/2005 | Cotteverte et al. |
| 2006/0200037 | A1 | 9/2006 | Falasco |
| 2007/0062255 | A1 | 3/2007 | Talton |
| 2007/0091941 | A1 | 4/2007 | Mori et al. |
| 2007/0133001 | A1 | 6/2007 | Cox et al. |
| 2008/0091085 | A1 | 4/2008 | Urushihata et al. |
| 2008/0139021 | A1 | 6/2008 | Suzuki et al. |
| 2008/0170597 | A1 | 7/2008 | van der Veer |
| 2009/0201957 | A1 | 8/2009 | Brotherton-Ratcliffe |
| 2009/0306527 | A1 | 12/2009 | Kubo et al. |
| 2010/0002234 | A1 | 1/2010 | Cormier et al. |
| 2010/0074089 | A1 | 3/2010 | Smith et al. |
| 2011/0072887 | A1 | 3/2011 | Oki |
| 2011/0216311 | A1 | 9/2011 | Kachanov et al. |
| 2011/0269632 | A1 | 11/2011 | Haick |
| 2011/0295140 | A1 | 12/2011 | Zaidi et al. |
| 2012/0143805 | A1 | 6/2012 | Gold et al. |
| 2012/0250706 | A1 | 10/2012 | Stiens et al. |
| 2012/0266883 | A1 | 10/2012 | Taylor et al. |
| 2012/0309048 | A1 | 12/2012 | Ratcliffe et al. |
| 2013/0144561 | A1 | 6/2013 | Harb et al. |
| 2013/0303929 | A1 | 11/2013 | Martino et al. |
| 2014/0293283 | A1 | 10/2014 | Farooq et al. |
| 2014/0320856 | A1 | 10/2014 | McKeever et al. |
| 2015/0032019 | A1 | 1/2015 | Acker et al. |
| 2015/0335267 | A1 | 11/2015 | Cormier et al. |
| 2016/0174875 | A1 | 6/2016 | Forster et al. |
| 2016/0285236 | A1 | 9/2016 | Yvind |
| 2017/0074857 | A1 | 3/2017 | Dennis et al. |
| 2017/0119280 | A1* | 5/2017 | Ahmad ............... A61B 5/097 |
| 2018/0059003 | A1 | 3/2018 | Jourdainne |
| 2018/0156718 | A1 | 6/2018 | Fleisher et al. |
| 2018/0202918 | A1 | 7/2018 | Tanaka et al. |
| 2018/0202923 | A1 | 7/2018 | Kageyama et al. |
| 2018/0214050 | A1 | 8/2018 | Purves |
| 2018/0261974 | A1 | 9/2018 | Purves et al. |
| 2019/0113501 | A1* | 4/2019 | Jameson ............ G01N 33/497 |
| 2019/0265159 | A1 | 8/2019 | Koulikov |
| 2019/0265160 | A1 | 8/2019 | Koulikov |
| 2019/0271641 | A1 | 9/2019 | Koulikov |
| 2019/0301933 | A1 | 10/2019 | Allison |
| 2019/0323955 | A1 | 10/2019 | Koulikov |

FOREIGN PATENT DOCUMENTS

| | | |
|---|---|---|
| CN | 101470072 A | 7/2009 |
| CN | 102316801 B | 1/2012 |
| CN | 102798631 A | 11/2012 |
| CN | 102841082 A | 12/2012 |
| CN | 102264292 B | 5/2014 |
| CN | 106908389 A | 6/2017 |
| CN | 107037003 A | 8/2017 |
| CN | 109856054 A | 6/2019 |
| DE | 2130331 A1 | 3/1977 |
| DE | 2723939 A1 | 12/1978 |
| DE | 3819687 A1 | 12/1989 |
| DE | 10156149 A1 | 6/2003 |
| EP | 557658 A1 | 9/1993 |
| EP | 600711 A2 | 6/1994 |
| EP | 1535047 B1 | 6/2005 |
| EP | 1304955 B1 | 12/2008 |
| EP | 1997198 B1 | 6/2012 |
| EP | 1418842 B1 | 7/2012 |
| EP | 3037805 A1 | 6/2016 |
| EP | 2745097 B1 | 2/2018 |
| EP | 3419122 A1 | 12/2018 |
| EP | 3467473 A1 | 4/2019 |
| GB | 1019295 | 2/1966 |
| JP | 2001194299 A | 7/2001 |
| JP | 2006189392 A | 7/2006 |
| JP | 2006226727 A | 8/2006 |
| JP | 2010243270 A | 10/2010 |
| JP | 2013011620 A | 1/2013 |

(56) References Cited

FOREIGN PATENT DOCUMENTS

| JP | 5341519 B2 | 11/2013 |
|---|---|---|
| JP | 5537174 B2 | 7/2014 |
| JP | 2016503904 A | 2/2016 |
| WO | 2090935 | 11/2002 |
| WO | 2005038436 A2 | 4/2005 |
| WO | 2005076875 A2 | 8/2005 |
| WO | 2005088274 A1 | 9/2005 |
| WO | 2017142644 A1 | 12/2007 |
| WO | 2011117572 A1 | 9/2011 |
| WO | 2012004794 A1 | 1/2012 |
| WO | 2014070952 A1 | 5/2014 |
| WO | 2018142027 A1 | 8/2018 |
| WO | 2019239827 A1 | 12/2019 |

OTHER PUBLICATIONS

ISR for PCT/CA2007/002306 mailed Apr. 17, 2008.
Office action for CA2671122 dated Jun. 13, 2011.
Harren et al., Photoacoustic Spectroscopy in Trace Gas Monitoring, encyclopedia of Analytical Chemistry, pp. 2203-2226, J. Wiley and Sons, 2000.
Freed, C., Status of CO2 Isotope Lasers and Their Applications in Tumable Laser Spectroscopy, IEEE Journal of Quantum Electronics, vol. QE-18, No. 8, 1982.
Sharpe et al., "Gas Phase Databases for Quantitative Infrared Spectroscopy," Applied Spectroscopy, vol. 58, No. 12, 2004.
Akaike, H., "A new look at the statistical model identification," IEEE Transactions on Automatic Control, 19(6): 716-723, 1974.
Cormier, John G., "Development of an Infrared Cavity Ringdown Spectroscopy Experiment and Measurements of Water Vapor Continuum Absorption.," Thesis, 2002.
Kurochkin et al., "Three Mirror Cavity CO2 Lser for Inactivity Saturated-Absorption Spectroscopy." Optical Spectroscopy, vol. 65, No. 2, pp. 265-267, Aug. 1988.
Office Action for U.S. Appl. No. 12/517,036 dated Dec. 14, 2011.
Fuchs, D., et al., "Decline of exhaled isoprene in lung cancer patients correlates with immune activation," Journal of breath research 6.2 (2012): 027101+B8.
Ligor, Magdalena, et al., "Determination of volatile organic compounds of exhaled breath of patients with lung cancer using solid phase microextraction and gas chromatography mass spectrometry," Clinical chemistry and laboratory medicine 47.5 (2009): 550-560.
Vaughan, Christina, et al., "Automated determination of seven phenolic compounds in mainstream tobacco smoke," Nicotine and Tobacco Research 10.7 (2008): 1261-1268.
Cope, et al., "Effects of ventilation on the collection of exhaled breath in humans," J. App I Physiol 96: 1371-1379: 2004.
Office action for U.S. Appl. No. 14/720,447 dated Apr. 6, 2017.
Office action for U.S. Appl. No. 14/720,447 dated Apr. 19, 2018.
Final office action for U.S. Appl. No. 14/720,447 dated Sep. 13, 2017.
English translation of DE102013215640A1.
Office action for U.S. Appl. No. 14/720,456 dated Jun. 14, 2017.
Office action for U.S. Appl. No. 15/920,212 dated Jun. 27, 2019.
Final Office action for U.S. Appl. No. 15/920,212 dated Oct. 3, 2019.
Notice of Allowance for U.S. Appl. No. 15/920,212 dated Jan. 23, 2020.
International Search Report and Written Opinion for PCT/CA2020/050252 dated May 12, 2020.
International Search Report and Written Opinion for PCT/CA2020/050250 dated May 22, 2020.
International Search Report and Written Opinion for PCT/CA2020/050/249 dated Apr. 29, 2020.
International Search Report and Written Opinion for PCT/CA2020/050248 dated Jun. 11, 2020.
Office action for U.S. Appl. No. 15/917,225 dated Mar. 9, 2020.
Office action for U.S. Appl. No. 15/917,225 dated May 14, 2020.

* cited by examiner

APPARATUS AND METHOD FOR COLLECTING A BREATH SAMPLE USING A CONTAINER WITH CONTROLLABLE VOLUME

FIELD

The specification relates generally to sample collection systems, and more particularly to apparatuses and methods for collecting a breath sample.

BACKGROUND OF THE DISCLOSURE

Breath sample collection has traditionally been performed by collecting breath from a patient in a large container. The breath sample is then extracted from the container and transferred directly to an analyzer.

More recently, breath samples have been collected in breath sample storage devices known as sorbent tubes or thermal desorption tubes. Sorbent tubes are tubes containing a solid adsorbent material having a large surface area. When a gaseous sample is passed through a sorbent tube, some of the constituents, such as oxygen and carbon dioxide, flow through and out the other end of the sorbent tube, whereas other constituents are adsorbed by the adsorbent material. This enables many of the constituents of a breath sample to be captured by the adsorbent material while allowing the most voluminous constituents to flow through, thereby condensing the breath sample. As a result, most of the constituents of the breath sample can be collected within a much smaller volume.

Devices that allow these sorbent tubes to be filled directly by a person suffer from a number of issues, however. Within human breath is a significant amount of humidity that can interfere with this mode of breath collection. The humidity can form condensation on the inside of the conduits directing the breath to the sorbent tubes. This condensation attracts many of the constituents of breath, which freely adhere to the water molecules. As a result, many of the breath sample constituents do not make it to the sorbent tube and are thus not represented in the at least some of the breath sample that is analyzed.

Another issue is that sorbent tubes capture the constituents of breath more effectively at certain flow rates of breath through the sorbent tubes. The rate at which breath is flowed through the sorbent tubes in state-of-the-art devices is driven by the rate at which breath is blown into these devices by the person. This leads to a loss of parts of the breath sample.

SUMMARY OF THE DISCLOSURE

In one aspect, there is provided an apparatus for collecting a breath sample, comprising: a breath input interface configured to receive exhaled breath; a container connected to the breath input interface for storing at least some of the breath; and at least one controller configured to control a flow of the at least some of the breath from the container to at least one sorbent tube connected to the container asynchronous of when the breath is received.

The container can have a cavity in which the at least some of the breath is stored, a volume of the cavity being controllable. The volume of the cavity can be controllable by the at least one controller. The container can include a piston chamber that has a piston positioned therein, a position of the piston controlling the volume of the cavity. The at least one controller can be configured to actuate the piston to increase the volume of the cavity as the at least some of the exhaled breath is being received.

The apparatus can further include: a valve intermediate the breath input interface and the container; a first conduit system connecting the breath input interface and the valve; and a second conduit system connecting the container to the at least one sorbent tube. The at least one controller can be configured to control the valve to close and control actuation of the piston to impel the at least some of the breath through a subset of the at least one sorbent tube. A tube inlet valve can be positioned between the container and each of the at least one sorbent tube. The at least one controller can be configured to control each of the at least one tube inlet valve to select the subset of the at least one sorbent tube through which the at least some of the breath is flowed.

The subset can be a first subset, the apparatus can further include an inlet valve positioned along the second conduit system between an inlet and the container, the at least one controller can be configured to open the inlet valve and control actuation of the piston to draw air through the inlet and into the cavity, and the at least one controller can be configured to close the inlet valve and impel the intaken air from the cavity through the second conduit system. The at least one controller can control actuation of the piston to impel the intaken air through a second subset of the at least one sorbent tube. A tube inlet valve can be positioned between the container and each of the at least one sorbent tube. The at least one controller can be configured to control each of the at least one tube inlet valve to select the second subset of the at least one sorbent tube through which the intaken air is flowed through.

The container can include an at least partially flexible collapsible receptacle. The apparatus can further comprise: a valve intermediate the breath input interface and the container; a first conduit system connecting the breath input interface and the valve; and a second conduit system connecting the container to the at least one sorbent tube. The apparatus can further include a pump controlled by the at least one controller to impel the at least some of the breath from the container through a subset of the at least one sorbent tube. A tube inlet valve can be positioned between the container and each of the at least one sorbent tube. The at least one controller can be configured to control each of the at least one tube inlet valve to select the subset of the at least one sorbent tube through which the at least some of the breath is flowed.

The pump can be positioned between the valve and the container, and the at least one controller can be configured to control the pump to draw the at least some of the exhaled breath into the container.

The subset can be a first subset, the apparatus can further include an inlet valve positioned along the second conduit system between an inlet and the container, and the at least one controller can be configured to close the inlet valve and control the pump to flow air from the container through a second subset of the at least one sorbent tube. The at least one controller can be configured to open the inlet valve and control the pump to flow air through the inlet and into the cavity. A tube inlet valve can be positioned between the container and each of the at least one sorbent tube. The at least one controller can be configured to control each of the at least one tube inlet valve to select the first subset of the at least one sorbent tube through which the at least some of the breath is flowed.

The apparatus can further comprise: a valve intermediate the breath input interface and the container; and a first conduit system connecting the breath input interface and the valve. The at least one controller can be configured to control the valve to close and control the volume of the container to impel the at least some of the breath through a subset of the at least one sorbent tube upon capturing a target volume of the breath in the container. The at least one controller can be configured to control the volume of the container to decrease at one of at least two breath flow rates at which the at least one controller can control the volume of the container to impel the breath through the subset of the at least one sorbent tube.

In another aspect, there is provided a method of collecting a breath sample, comprising: receiving exhaled breath via a breath input interface; storing at least some of the breath in a container connected to the breath input interface; and controlling, via at least one controller, a flow of the at least some of the breath from the container to at least one sorbent tube connected to the container asynchronous of when the exhaled breath is received.

The storing can comprise storing the at least some of the exhaled breath in a cavity of the container, and a volume of the cavity can be controllable. The method can further include controlling the volume of the cavity via the at least one controller. The method can further include actuating, via the at least one controller, a piston positioned in a piston chamber of the container, a position of the piston controlling the volume of the cavity. The method can further comprise actuating the piston to increase the volume of the cavity as the at least some of the exhaled breath is being received. The method can further include controlling a flow of the at least some of the exhaled breath via a valve intermediate the breath input interface and the container, wherein a first conduit system connects the breath input interface and the valve, and wherein a second conduit system connects the container to the at least one sorbent tube. The method can further include: controlling the valve via the at least one controller to close; and controlling actuation of the piston to impel the at least some of the breath through a subset of the at least one sorbent tube. A tube inlet valve can be positioned between the container and each of the at least one sorbent tube, and the method can further include controlling each of the at least one tube inlet valve to select the subset of the at least one sorbent tube through which the at least some of the breath is flowed.

The method can further include: controlling, via the at least one controller, the valve to close; controlling an inlet valve separating the container from an inlet to open; controlling actuation of the piston to draw air through the inlet and into the cavity; controlling the inlet valve to close; and controlling actuation of the piston to impel the intaken air from the cavity through the second conduit system.

The method can further include controlling actuation of the piston to impel the intaken air through a second subset of the at least one sorbent tube. A tube inlet valve can be positioned between the container and each of the at least one sorbent tube. The method can further include controlling each of the at least one tube inlet valve to select the second subset of the at least one sorbent tube through which the intaken air is flowed through.

The container can include an at least partially flexible collapsible receptacle. The method can further include controlling a flow of the at least some of the breath via a valve intermediate the breath input interface and the container, wherein a first conduit system connects the breath input interface and the valve, and wherein a second conduit system connects the container to the at least one sorbent tube. The method can further include controlling a pump to flow the at least some of the breath from the container through a subset of the least one sorbent tube. A tube inlet valve can be positioned between the container and each of the at least one sorbent tube. The method can further comprise controlling each of the at least one tube inlet valve to select the subset of the at least one sorbent tube through which the at least some of the breath is flowed.

The pump can be positioned between the valve and the container, and the method can further include controlling the pump to draw the at least some of the exhaled breath into the container.

The subset can be a first subset, and the method can further include: closing the valve; opening an inlet valve intermediate an inlet and the container; and controlling the pump to flow air through a second subset of the at least one sorbent tube. The method can further include: opening the inlet valve; and controlling the pump to flow air through the inlet and into the cavity. A tube inlet valve can be positioned between the container and each of the at least one sorbent tube. The method can further include controlling each of the at least one tube inlet valve to select the subset of the at least one sorbent tube through which the at least some of the breath is flowed.

The method can further include controlling a flow of the exhaled breath from a first conduit system to which the breath input interface is connected through to the container via a valve. The method can further include: controlling the valve to close; and controlling the volume of the container to flow the at least some of the breath through a subset of the at least one sorbent tube upon capturing a target volume of the breath in the container. During the controlling the volume, the volume can be controlled to decrease at one of at least two breath flow rates at which the volume can be controlled to decrease at to impel the breath through the subset of the at least one sorbent tube.

In a further aspect, there is provided an apparatus for collecting a breath sample, comprising: a breath input interface configured to receive exhaled breath; a metering device configured to determine a constituent level in the breath being received; a first conduit system extending from the breath input interface and connected to at least one breath sample storage device; a valve positioned along the first conduit system to control a flow of the exhaled breath towards the at least one breath sample storage device; and at least one controller configured to determine if the constituent level is within a constituent level target range, determine if a change rate in the constituent level is within a constituent level change rate target range, and control the valve to open at least partially based on whether the constituent level is within the constituent level target range and the change rate is within the constituent level change rate target range.

The metering device can be a capnometer, the constituent level can be a carbon dioxide level, the constituent level target range can be a carbon dioxide level target range, and the constituent level change rate target range can be a carbon dioxide level change rate target range. The apparatus can further include a flow meter configured to determine a flow rate of the exhaled breath being received, wherein the at least one controller is configured to control the valve to open at least partially based on the determined flow rate being within a flow rate target range. The apparatus can further include a display, wherein the at least one controller is configured to control the display to present flow rate notifications thereon.

The apparatus can further include at least one light element, wherein the at least one controller is configured to control the at least one light element to present flow rate notifications therewith.

The apparatus can further include a speaker, wherein the at least one controller is configured to control the speaker to play audible flow rate notifications therethrough.

The constituent level target range can extend between a constituent level minimum threshold and an infinite upper bound.

The constituent level change rate target range can extend between an infinite lower bound and a constituent level change rate maximum threshold.

The flow rate target range can extend between a minimum flow rate threshold and an infinite upper bound.

The at least one controller can be configured to monitor the constituent level after opening the valve.

The apparatus can further include a flow meter configured to determine a flow rate of the exhaled breath being received, wherein the at least one controller is configured to monitor the flow rate after opening the valve, and control the valve to close at least partially based on the determined flow rate being within a flow rate termination range.

In yet another aspect, there is provided a method for collecting a breath sample, comprising: receiving exhaled breath via a breath input interface from which a first conduit system extends towards at least one breath sample storage device, wherein a valve is positioned to control travel of the exhaled breath from the first conduit system towards the at least one breath sample storage device; determining, via at least one controller, if a constituent level in the exhaled breath being received is within a constituent level target range; determining a change rate in the constituent level is within a constituent level change rate target range; and controlling the valve to open at least partially based on whether the constituent level is within the constituent level target range and the change rate is within the constituent level change rate target range.

The constituent level can be a carbon dioxide level, the constituent level target range can be a carbon dioxide level target range, and the constituent level change rate target range can be a carbon dioxide level change rate target range.

The method can further include determining a flow rate of the exhaled breath being received, wherein the capturing is performed at least partially based on the determined flow rate being within a flow rate target range. The method can further include controlling a display to present flow rate notifications thereon. The method can further include controlling at least one light element to present flow rate notifications therewith.

The method can further include control a speaker to play audible flow rate notifications therethrough.

The carbon dioxide level target range can extend between a carbon dioxide level minimum threshold and an infinite upper bound.

The carbon dioxide level change rate target range can extend between an infinite lower bound and a carbon dioxide level change rate maximum threshold.

The flow rate target range can extend between a minimum flow rate threshold and an infinite upper bound.

The method can further include monitoring the carbon dioxide level after opening the valve.

The method can further include determining a flow rate of the exhaled breath being received, wherein the at least one controller is configured to monitor the flow rate after opening the valve, and control the valve to close at least partially based on the determined flow rate being within a flow rate termination range.

In still another aspect, there is provided an apparatus for collecting a breath sample, comprising: a breath input interface configured to receive exhaled breath; a first conduit system connected to the breath input interface; a valve configured to control fluid communication between the first conduit system and at least one breath sample storage device configured to store a breath sample; an air circulation system configured to circulate air through the first conduit system upon completion of a first received exhaled breath; and at least one controller configured to control the valve upon completion of the first received exhaled breath at least partially based on a humidity level in the first conduit system.

The at least one controller can be configured to control the valve at least partially based on whether a change rate in the humidity level is within a humidity level change rate target range. The at least one controller can be configured to close the valve to inhibit passage of a subsequent exhaled breath from the first conduit system to the at least one breath sample storage device until the change rate in the humidity level within the first conduit system is within the humidity level change rate target range. The apparatus can further include a hygrometer connected to the first conduit system and configured to determine the humidity level in the first conduit system. The apparatus can further include a notification system for indicating when the change rate in the humidity level within the first conduit system is within the humidity level change rate target range.

The first conduit system can include a breath intake conduit extending between the breath input interface and the valve, and the hygrometer can be connected to an exhaust conduit of the first conduit system that branches from the breath intake conduit. The fluid circulation system can be directly connected to the exhaust conduit. The exhaust conduit can include a flow meter configured to measure a flow rate along the exhaust conduit.

The at least one controller can be configured to control the valve at least partially based on whether the humidity level is within a humidity level target range. The at least one controller can be configured to close the valve to inhibit passage of a subsequent exhaled breath from the first conduit system to the at least one breath sample storage device until the humidity level within the first conduit system is within the humidity level target range.

In another aspect, there is provided a method for collecting a breath sample, comprising: receiving an exhaled breath via a breath input interface connected to a first conduit system; collecting at least some of the exhaled breath via at least one breath sample storage device connected to the first conduit system; detecting a completion of the exhaled breath; closing a valve between the first conduit system and the at least one sorbent tube upon detecting the completion of the exhaled breath; circulating air through a first conduit system connected to the breath input interface after detecting the completion of the exhaled breath; monitoring a humidity level in the first conduit system; and controlling, via at least one controller, the valve at least partially based on the humidity level in the first conduit system.

The controlling can include determining if a change rate in the humidity level is within a humidity level change rate target range. The method can further include controlling the valve to close to inhibit passage of a subsequently exhaled breath from the first conduit system to the at least one breath sample storage device until the change rate in the humidity level within the first conduit system is within the humidity level change rate target range. The method can further include determining the humidity level in the first conduit system via a hygrometer connected to the first conduit system. The method can further include indicating when the change rate in the humidity level is within the humidity level change rate target range.

The first conduit system can include a breath intake conduit extending between the breath input interface and the valve, and wherein the determining of the humidity level is performed by a hygrometer connected to an exhaust conduit of the first conduit system that branches from the breath intake conduit. The fluid circulation system can be directly connected to the exhaust conduit. The method can further include measuring a flow rate along the exhaust conduit via a flow meter along the exhaust conduit.

The controlling can include determining if the humidity level is within a humidity level target range. The method can further include controlling the valve to close to inhibit passage of a subsequently exhaled breath from the first conduit system to the at least one breath sample storage device until the humidity level within the first conduit system is within the humidity level target range.

In a further aspect, there is provided an apparatus for collecting a breath sample, comprising: a breath input interface configured to receive exhaled breath; a first conduit system connected to the breath input interface; at least one breath sample storage device connected to the breath input interface via a breath intake conduit of the first conduit system extending between the breath input interface and the breath collection system, the at least one breath sample storage device being configured to capture at least some of the breath; and at least one metering device for measuring at least one characteristic, the at least one metering device being positioned along an exhaust conduit of the first conduit system that branches from the breath intake conduit.

The at least one metering device can include a flow meter that measures a flow rate of the exhaled breath along the exhaust conduit of the first conduit system. The at least one metering device can include a capnometer positioned along the exhaust conduit of the first conduit system to measure a carbon dioxide level in the exhaled breath.

The at least one metering device can include a hygrometer positioned along the exhaust conduit of the first conduit system to measure a humidity level in the exhaled conduit. The apparatus can further include a pump positioned along the exhaust conduit of the first conduit system to flow air through the exhaust conduit.

In yet another aspect, there is provided a method for collecting a breath sample, comprising: receiving exhaled breath via a breath input interface; a first conduit system connected to the breath input interface; capturing breath via a breath collection system that is connected to the breath input interface via a breath intake conduit of a first conduit system extending between the breath input interface and the breath collection system; and measuring at least one characteristic along an exhaust conduit of the first conduit system that branches from the breath intake conduit via at least one metering device positioned along the exhaust conduit.

The at least one metering device can include a flow meter, and the at least one characteristic can include a flow rate of the exhaled breath along the exhaust conduit.

The at least one metering device can include a capnometer, and the at least one characteristic can include a carbon dioxide level of the exhaled breath.

The method can further include determining a humidity level along the exhaust conduit via a hygrometer positioned along the exhaust conduit of the first conduit system.

The method can further include flowing air through the exhaust conduit via a pump positioned along the exhaust conduit.

In still yet another aspect, there is provided an apparatus for collecting a breath sample, comprising: a breath input interface configured to receive exhaled breath; a container connected to the breath input interface for receiving at least some of the exhaled breath, the container having a cavity with a volume that is controllable; and at least one controller configured to control the volume of the cavity to increase at a volume increase rate that is at most equal to a flow rate of the exhaled breath received by the breath input interface.

A breath intake conduit of a first conduit system can extend from the breath input interface and towards the container, and an exhaust conduit of the first conduit system can branch from the breath collecting portion at a first end thereof and has an outlet at a second end thereof. The apparatus can further include a flow meter positioned to measure a flow rate along the exhaust conduit. The volume increase rate of the volume of the container can be proportional to the flow rate along the exhaust conduit. The volume of the container can be directly mechanically controllable by the at least one controller. The container can include a piston chamber having an actuatable piston positioned therein, a position of the piston in the piston chamber defining the volume of a cavity. The apparatus can further include a valve positioned to control travel of the exhaled breath to the piston chamber. The apparatus can further include at least one sorbent tube connected to the container, wherein the at least one controller is configured to control the valve to close and control actuation of the piston to impel the breath in the cavity through the at least one sorbent tube.

The container can include an at least partially flexible collapsible receptacle, and the apparatus can further include a pump configured intermediate the breath input interface and the container to impel the breath into the at least partially flexible collapsible receptacle at the volume increase rate. The apparatus can further include at least one sorbent tube connected to the at least partially flexible collapsible receptacle, wherein the at least one controller is configured to control the pump to impel the breath in the cavity through a subset of the at least one sorbent tube. The apparatus can further include a valve positioned to control travel of the exhaled breath to the piston chamber.

The apparatus can further include a valve positioned to control travel of the exhaled breath to the piston chamber. The apparatus can further include a metering device positioned to determine a constituent level in the exhaust conduit, and the at least one controller can be configured to determine if the constituent level is within a constituent level target range, determine if a change rate in the constituent level is within a constituent level change rate target range, and control the valve to open at least partially based on whether the constituent level is within the constituent level target range and the change rate is within the constituent level change rate target range. The metering device can be a capnometer, the constituent level can be a carbon dioxide level, the constituent level target range can be a carbon dioxide level target range, and the constituent level change rate target range can be a carbon dioxide level change rate target range.

The apparatus can further include: a breath intake conduit of a first conduit system extending from the breath input interface and towards the container; and a flow meter positioned to measure a flow rate of the exhaled breath along the breath intake conduit. The volume increase rate of the volume of the container can be proportional to the flow rate along the breath intake conduit. The volume of the container can be directly mechanically controllable by the at least one controller. The container can include a piston chamber having an actuatable piston positioned therein, a position of the piston in the piston chamber defining the volume of a cavity. The apparatus can further include a valve positioned to control travel of the exhaled breath to the piston chamber. The apparatus can further include at least one sorbent tube connected to the container, wherein the at least one controller is configured to control the valve to close and control actuation of the piston to impel the breath in the cavity through a subset of the at least one sorbent tube.

The container can include an at least partially flexible collapsible receptacle, and the apparatus can further include a pump configured intermediate the breath input interface and the container to impel the breath into the at least partially flexible collapsible receptacle at the volume increase rate.

In still yet another aspect, there is provided a method for collecting a breath sample, comprising: receiving exhaled breath via a breath input interface; storing at least some of the exhaled breath in a container connected to the breath input interface, the container having a cavity with a volume that is controllable; and controlling, via at least one controller, the volume of the container to increase at a volume increase rate that is at most equal to a flow rate of the exhaled breath received by the breath input interface.

A breath intake conduit of a first conduit system can extend from the breath input interface and towards the container, and an exhaust conduit of the first conduit system can branch from the breath collecting portion at a first end thereof and has an outlet at a second end thereof. The method can further include measuring a flow rate along the exhaust conduit via a flow meter. The volume increase rate of the volume of the container can be proportional to the flow rate. The method can further include directly mechanically controlling the volume of the container. The container can include a piston chamber in which a piston is positioned, the position of the piston defining the volume of a cavity, and wherein the directly mechanically controlling comprises actuating the piston. The method can further include travel of the exhaled breath to the piston chamber via a valve positioned between the breath input interface and the container. The method can further include: controlling the valve to close; and controlling actuation of the piston to impel the breath in the cavity through at least one sorbent tube connected to the container.

The container can include an at least partially flexible collapsible receptacle, and the method can further include impelling, via a pump intermediate the breath input interface and the container, the exhaled breath into the at least partially flexible collapsible receptacle at the volume increase rate.

The method can further include controlling the pump to impel the breath in the cavity through a subset of at least one sorbent tube connected to the at least partially flexible collapsible receptacle. The method can further include controlling travel of the exhaled breath to the piston chamber via a valve.

The method can further include controlling travel of the exhaled breath to the piston chamber via a valve. The method can further include: determining a constituent level in the exhaust conduit; comparing, via the at least one controller, the constituent level to a constituent level target range; comparing a change rate in the constituent level to a constituent level change rate target range; and control the valve to open at least partially based on whether the constituent level is within the constituent level target range and whether the change rate is within the constituent level change rate target range. The constituent level can be a carbon dioxide level, the constituent level target range can be a carbon dioxide level target range, and the constituent level change rate target range can be a carbon dioxide level change rate target range.

A breath intake conduit of a first conduit system can extend from the breath input interface and towards the container, and the method can further include measuring a flow rate of the exhaled breath along the breath intake conduit via a flow meter. The volume increase rate of the volume of the container can be proportional to the flow rate. The method can further include directly mechanically controlling the volume of the container by the at least one controller. The container can include a piston chamber having an actuatable piston positioned therein, and the method can further include actuating a position of the piston in the piston chamber defining the volume of a cavity. The method can further include controlling travel of the exhaled breath to the piston chamber via a valve. The method can further include: controlling the valve to close; and controlling actuation of the piston to impel the breath in the cavity through a subset of at least one sorbent tube connected to the container.

The container can include an at least partially flexible collapsible receptacle, and the method can further include impelling the breath into the at least partially flexible collapsible receptacle at the volume increase rate via a pump positioned intermediate the breath input interface and the container.

Other technical advantages may become readily apparent to one of ordinary skill in the art after review of the following figures and description.

BRIEF DESCRIPTIONS OF THE DRAWINGS

For a better understanding of the embodiment(s) described herein and to show more clearly how the embodiment(s) may be carried into effect, reference will now be made, by way of example only, to the accompanying drawings in which.

Figure 1:
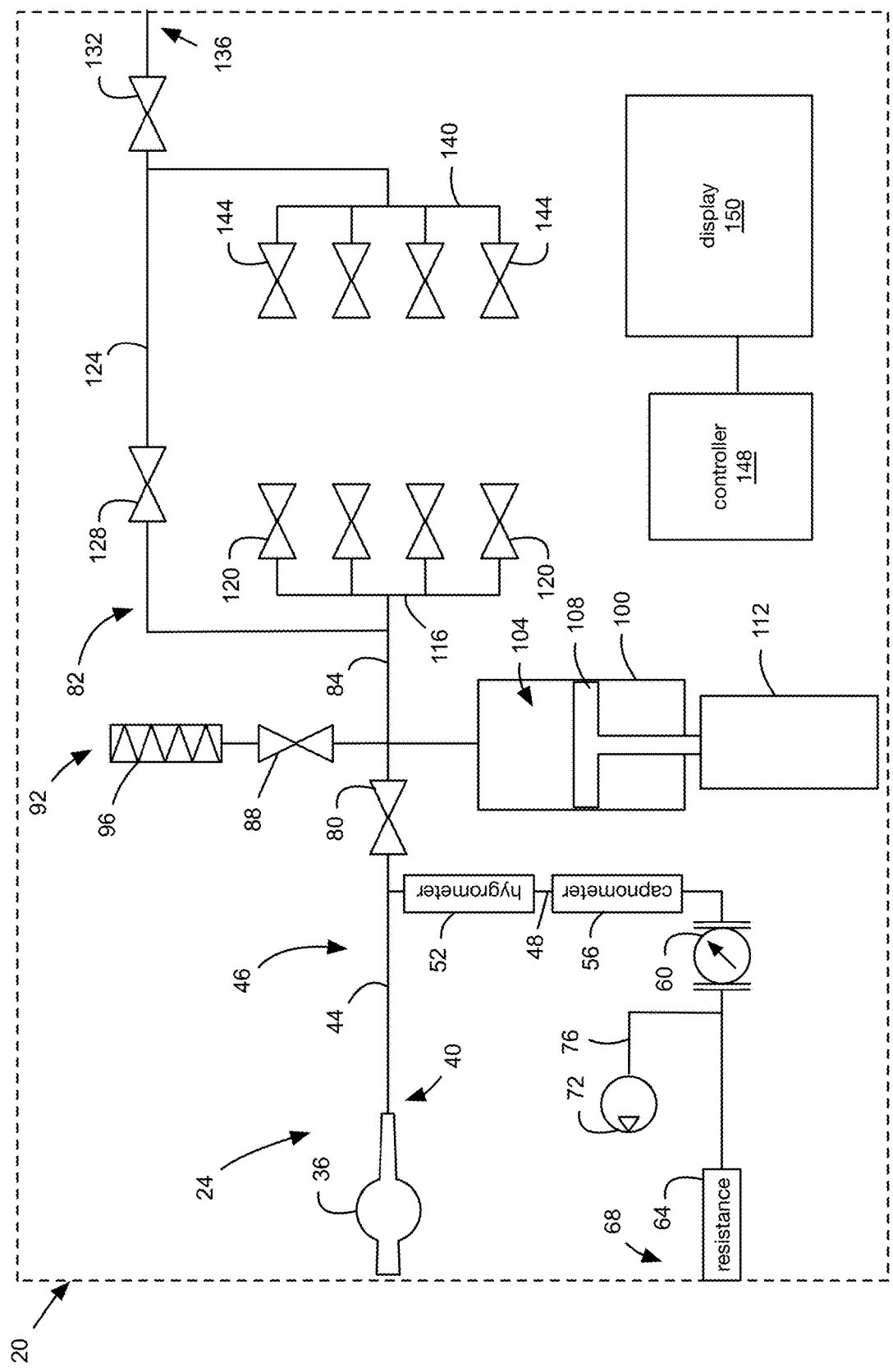
FIG. 1 shows a breath sample collection apparatus in accordance with one embodiment thereof.

Unless otherwise specifically noted, articles depicted in the drawings are not necessarily drawn to scale.

DETAILED DESCRIPTION

For simplicity and clarity of illustration, where considered appropriate, reference numerals may be repeated among the Figures to indicate corresponding or analogous elements. In addition, numerous specific details are set forth in order to provide a thorough understanding of the embodiment or embodiments described herein. However, it will be understood by those of ordinary skill in the art that the embodiments described herein may be practiced without these specific details. In other instances, well-known methods, procedures and components have not been described in detail so as not to obscure the embodiments described herein. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Modifications, additions, or omissions may be made to the systems, apparatuses, and methods described herein without departing from the scope of the disclosure. For example, the components of the systems and apparatuses may be integrated or separated.

Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

A breath sample collection apparatus 20 in accordance with an embodiment is shown in FIG. 1. The breath sample collection apparatus 20 enables a breath sample to be collected in sorbent tubes asynchronously of when exhaled breath is provided. The breath sample collection apparatus 20 includes a container for receiving exhaled breath. The breath is subsequently flowed through one or more sorbent tubes asynchronously of when the breath is received. The flowing of the breath through the one or more sorbent tubes can be performed by generating a positive relative pressure difference to impel the breath, by generating a negative relative pressure difference to draw the breath, or in any other suitable manner. As a result, the adsorption of the breath by the sorbent tubes can be controlled more stringently.

The breath sample collection apparatus 20 includes a breath input interface 24 for receiving exhaled breath from a person. The breath input interface 24 includes a mouthpiece 36 that is secured to a breath intake end 40 of a breath intake conduit 44 of a pre-collection conduit system 46.

The mouthpiece 36 is made of polypropylene or another suitably safe material that is preferably inexpensive so that it can be disposable/replaced. Further, preferably, the mouthpiece 36 does not off-gas volatile organic compounds ("VOCs") or off-gases VOCs at a low rate so that it does not significantly contaminate the breath sample. It can include a viral/bacterial filter to keep bacterium and particulates out of the sample. By making the mouthpiece 36 disposable, each patient can be provide with a new filter to avoid cross-contamination of the samples and passing on of viruses, bacteria, etc.

The polypropylene of the mouthpiece 36 is clear and will slightly fog up if humidity is high. This feature can be used to visibly detect condensation, as it can be undesirable to have condensation in the breath sample collection apparatus 20.

In other embodiments, the breath input interface can be constructed to receive breath from other animals.

The conduits of the breath sample collection apparatus 20 are made of stainless steel that is coated with an inert coating. The inert coating can be made of any suitably inert substance, such as a silica-based or quartz material.

An exhaust conduit 48 is connected to and branches from the breath intake conduit 44 at a first end thereof. A set of metering devices are positioned along the exhaust conduit 48, including a hygrometer 52 to measure the humidity in the exhaust conduit 48. Condensation can deteriorate the function of the breath sample collection apparatus 20 in that components of a person's breath can be trapped by this condensation, thus not being correctly represented in the collected breath sample. Further, certain levels of humidity and/or condensation can impact the function of other components of the breath sample collection apparatus 20. A capnometer 56 is positioned along the exhaust conduit 48 to measure the carbon dioxide content of a patient's breath. Also positioned along the exhaust conduit 48 is a flow meter 60 that determines the flow rate of the breath along the exhaust conduit 48. A low-pressure resistance portion 64 along the exhaust conduit 48 provides a low amount of resistance to the flow of gas along the exhaust conduit 48 towards an exhaust conduit outlet 68 at a second end of the exhaust conduit 48. The low-pressure resistance portion 64 acts as a cap on the exhaust conduit 48 and inhibits return diffusion gas from entering the exhaust conduit 48 while allowing gas to flow in both directions if needed. Any suitable structure can be employed to provide the low-pressure resistance portion 64, such as a flexible or hinged flap, a section of conduit having a restricted cross-section or change(s) in direction, etc.

An air circulation system includes a pump conduit 76 that branches from the exhaust conduit 48 and terminates at a pump 72 that is driven by a motor. The pump 72 is configured to draw ambient air in and through the exhaust conduit 48 and the breath intake conduit 44, such as via the mouthpiece 36, and expel it into the surrounding environment, when needed. Any fluid pump that is suitable for use with gases can be employed.

The inner diameter size of the mouthpiece 36 and the conduit portions 44, 48 are selected to provide only insignificant resistance to the exhalation of breath through the mouthpiece 36. Further, the conduit portions 44, 48 can be heated or cooled as desired to control the formation of condensation therealong. This can be desirable so that condensation is less likely to pass through to the breath sample collection devices, such as sorbent tubes.

A breath collection valve 80 is connected to the breath intake conduit 44 and controls the flow of a gas from the breath input interface 24 of the breath intake conduit 44 to a breath collection conduit 84 of the breath capture conduit system 82. The breath intake conduit 44 forms part of the direct path between the breath input interface 24 and the breath capture conduit system 82. An intake valve 88 controls the flow of gas entering or exiting the breath collection conduit 84 via an ambient air inlet 92. An air filter 96 is positioned between the ambient air inlet 92 and the intake valve 88 and filters incoming ambient air to inhibit the entry to particulate contamination therein.

A container is in fluid communication with the breath collection conduit 84 and is configured to store breath received from the breath collection conduit. The container in this embodiment includes a piston chamber 100 having a cavity 104 therein defined at least partially by interior walls of the piston chamber 100. The piston chamber 100 has a two-liter capacity and can have any suitable cross-sectional shape. A piston 108 corresponds in shape to and is positioned within the piston chamber 100 and is driven by a piston motor 112. The piston 108 seals against the sides of the piston chamber 100 to provide an airtight seal. The piston motor 112 can be any suitable type of motor to actuate the piston 108 within the piston chamber 100.

The volume of the cavity 104 is directly mechanically controllable by the positioning of the piston 108 within the piston chamber 100 by the piston motor 112. Further, the volume change rate of the cavity 104 is controllable by actuating the piston 108 within the piston chamber 100 at a corresponding rate to either increase the volume of the cavity 104, defining a volume increase rate, by moving further into the piston chamber 100, or decrease the volume of the cavity 104, defining a volume decrease rate, by moving further out of the piston chamber 100.

In another embodiment, the piston chamber is constructed with an interior space, and the piston has a similar profile to slidingly move through the interior space of the piston chamber.

The breath collection conduit 84 is connected to a tube manifold 116. The tube inlet manifold 116 branches to four tube inlet valves 120. A bypass conduit 124 branches from the breath collection conduit 84 and has a bypass valve 128 positioned along the bypass conduit 124 to prevent or allow the flow of gas therealong. An outlet valve 132 is positioned towards an outlet 136 and controls the flow of gas through the outlet 136. A tube outlet manifold 140 is connected to the bypass conduit 124 and branches to four tube outlet valves 144. The tube inlet valves 120 and the tube outlet valves 144 have connectors for receiving sorbent tubes. In other embodiments, the breath sample collection apparatus 20 can be configured to receive and use any number of sorbent tubes.

A controller 148 controls operation of the breath sample collection apparatus 20. The controller 148 is connected to the valves 80, 88, 120, 128, 132, and 144 to open and close these valves as described herein below. In other embodiments, the functionality of the controller 148 can be performed by two or more controllers.

A display 150 is controlled by the controller 148 to present instructions and information to a person, as well as metrics collected by the breath sample collection apparatus 20, such as the completeness of the procedure, the estimated amount of time remaining, etc.

The internal components with which the breath comes into contact are generally inert. The conduits and valves are made of stainless steel and have an inert coating. Sealing elements within the valves are made of FKM, a family of fluoroelastomer materials, or another suitable resilient material that has a very low rate of off-gassing. While the polypropylene mouthpiece 36 can off-gas, the level is within an acceptable tolerance level.

Figure 2:
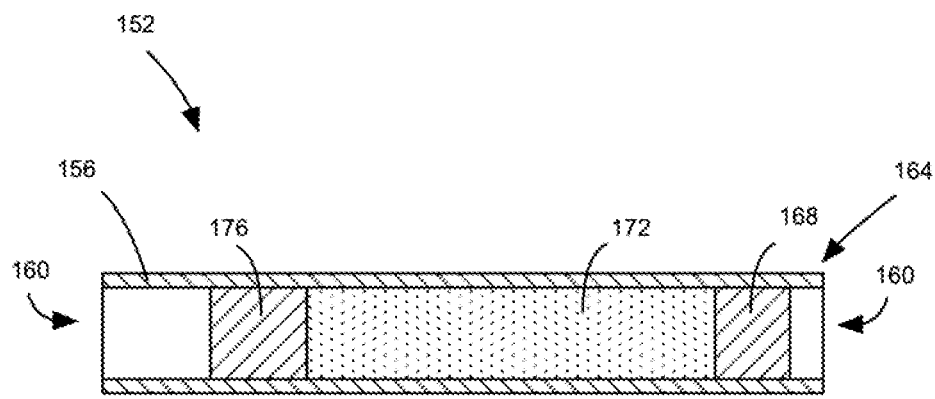
FIG. 2 shows a schematic diagram showing a sorbent tube for use with the apparatus of FIG. 1.

Referring now to FIG. 2, an exemplary sorbent tube 152 is shown. The sorbent tube 152 has a stainless-steel casing 156 that is tubular, defining an aperture 160 at each end thereof. A receiving end 164 of the sorbent tube 152 receives a gaseous fluid to be adsorbed. In the exemplary described embodiment, the gaseous fluid is human breath collected from a human for testing. A foam separator 168 is positioned towards the receiving end and is configured to distribute fluid pressure more evenly across the cross-section of the stainless-steel casing 156. An adsorbent material 172 is positioned adjacent to the foam separator 168 and another foam separator 110. The separators may alternatively be made of a wire mesh or other suitable material. The adsorbent material 172 is very porous, has a relatively high surface area, and is selected for sampling specific compounds to trap and retain the compounds of interest even in the presence of other compounds. Further, the adsorbent material 172 allows the collected compounds to be easily desorbed or extracted for analysis. In addition, the solid adsorbent which is selected does not react with the sample. In the particular example, the solid adsorbent is Tenax TA or a carbon material. As a gaseous fluid is received via the receiving end 164, the sample is more concentrated towards the receiving end 164 of the sorbent tube 152. In other embodiments, the composition and configuration of the sorbent tubes can vary, as will be appreciated by a person skilled in the art.

A method 200 of collecting a breath sample using the breath sample collection apparatus 20 will now be discussed with reference to FIGS. 1, 3, and 4A to 4G.

The method 200 commences with the drawing in of ambient air into the system (210). The system is flushed of any stale residual air by drawing ambient air in and then expelling it through the conduits 44, 48, 68, 76, 84, and 124. This is done to ensure that there is no cross-contamination from breath from a previous person with breath being presently collected. Stale room air in the system is replaced with fresh room air during this flush.

First, it is ensured that the valves 80, 120, and 128 are closed. Then the controller 148 directs the intake valve 88 to open, and the piston motor 112 to operate to withdraw the piston 108 in the piston chamber 100. As the piston 108 is withdrawn in the piston chamber 100, the cavity 104 defined by the interior walls of the piston chamber 100 and the piston 108 which is airtight sealed thereagainst increases in volume. As a result, the pressure within the cavity 104 rapidly decreases. Ambient air is drawn in through the ambient air inlet and the air filter 96, and into the cavity 104.

Figure 4A:
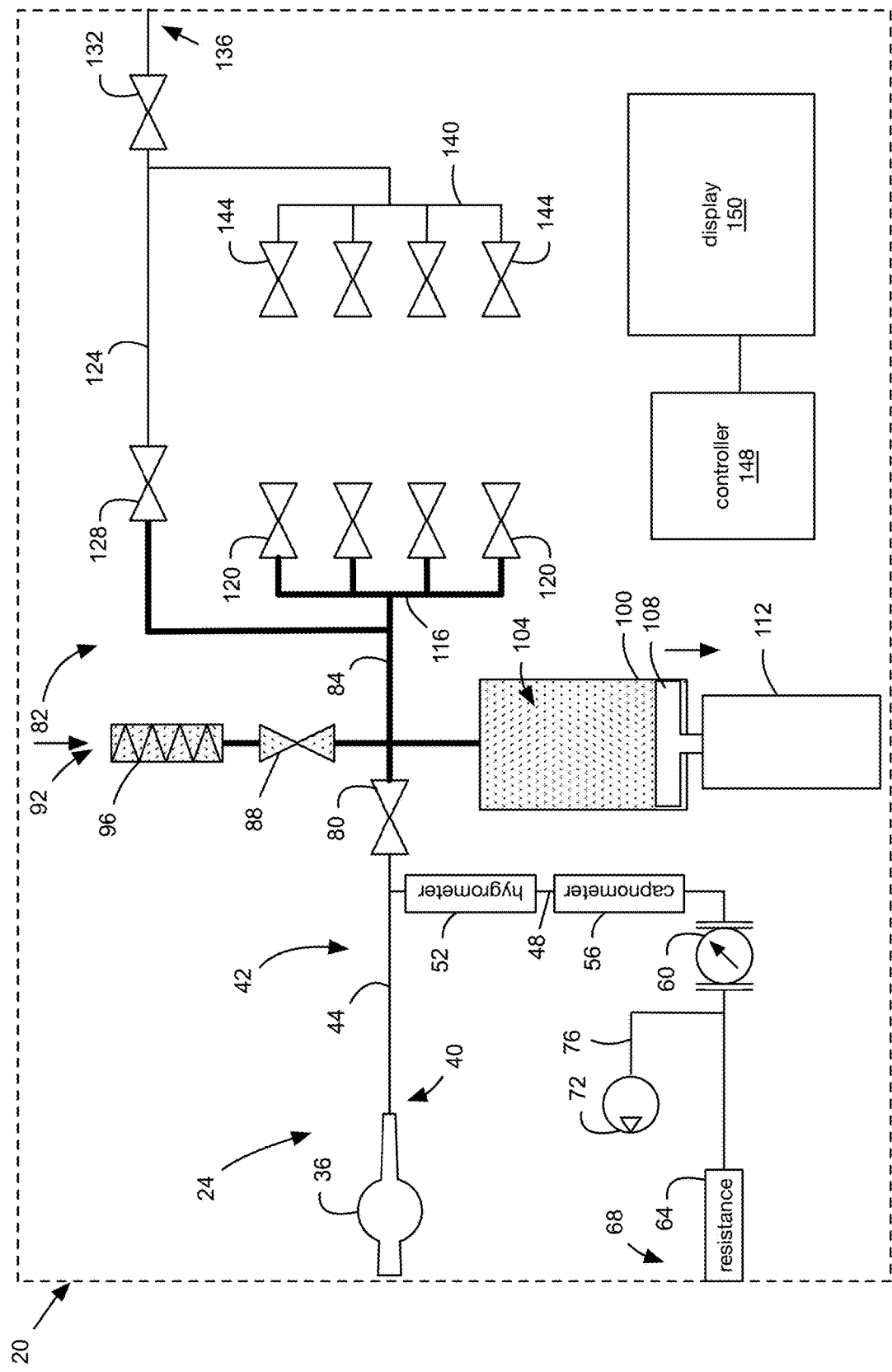
FIG. 4A shows the breath sample collection apparatus of FIG. 1, wherein ambient air is being drawn in to a piston chamber.

FIG. 4A shows the cavity 104 filled with ambient air that has been drawn in. For purposes of illustration hereinafter, valves that are open will include stippling and valves that are closed will be free of stippling. The air filter 96 removes particulate from the ambient air as it is drawn in and before it enters the breath collection conduit 84. While the breath collection valve 80 is closed during this intake of ambient air, traces of breath from a previous person may be present along the breath intake conduit 44 and along the exhaust conduit 48. It is desirable to maintain the breath collection valve 80 closed so that only ambient air with drawn in and so that it is filtered via the air filter 96.

Upon drawing the ambient air into the piston chamber 100, the ambient air is used to flush the system (208). The controller, upon withdrawing the piston 108 in the piston chamber 100, closes the intake valve 88 and then opens all the other valves. Once the valves 80, 120, 128, 132, and 144 have been opened, the controller 148 directs the piston motor 112 to drive the piston 108 into the piston chamber 100 to force the ambient air therein through the breath intake conduit 44 and out the mouthpiece 36, through the exhaust conduit 48 and out the exhaust conduit outlet 68, through the breath collection conduit 84 and the tube inlet manifold 116 and out the tube inlet valves 120, and through the bypass conduit 124 and the tube outlet manifold 140 and out the outlet 136 and the tube outlet valves 144.

As a result, the conduits of the system are effectively filled with ambient air.

Figure 4B:
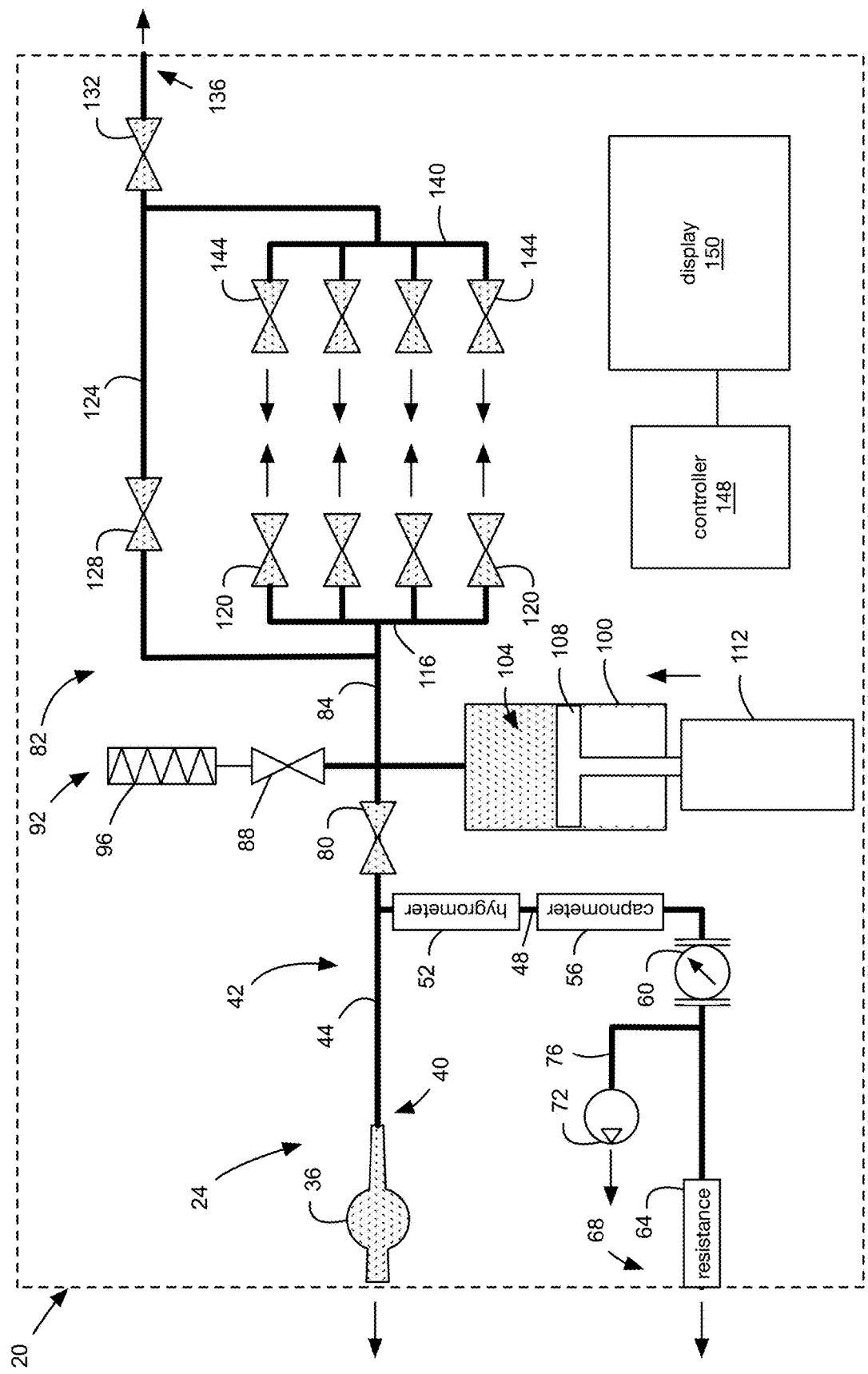
FIG. 4B shows the breath sample collection apparatus of FIG. 4A during flushing of the apparatus with the ambient air.

FIG. 4B shows the flushing of the breath sample collection apparatus 20.

After the system has been flushed with ambient air, the valves 80, 120, 132, and 144 are closed again.

Upon completing the flush, the controller 148 determines if the flush is to be repeated (212). The flush is repeated five to ten times, with about ten to 20 liters of air to reduce the probability of breath from a previous person contaminating the breath sample to be taken. If it is determined that the required number of flushes has not yet been completed, the controller 148 commences the process of drawing in ambient air again at 204.

If, instead, it is determined that sufficient flushes have been performed, one or more sorbent tubes 152a to 152d (alternatively, collectively referred to hereinafter as sorbent tubes 152) are loaded into the breath sample collection apparatus 20 (213). The bypass valve 128 and the outlet valve 132 are closed. One to four sorbent tubes 152 are then loaded into the breath sample collection apparatus 20.

In this embodiment, samples of ambient air are used as controls to which the breath sample can be compared. The ambient air that is breathed in by a person during the providing of a breath sample may contain some compounds that will register during analysis of the breath sample. In order to identify these compounds in the ambient air in the space in which the breath sample collection apparatus 20 is situated, ambient air can be adsorbed in one or more sorbent tubes 152. The breath sample collection apparatus 20 performs ambient air collection in a somewhat similar manner to breath collection. Thus, at least two sorbent tubes 152 are loaded so that at least one can capture ambient and at least another can capture breath.

Figure 4C:
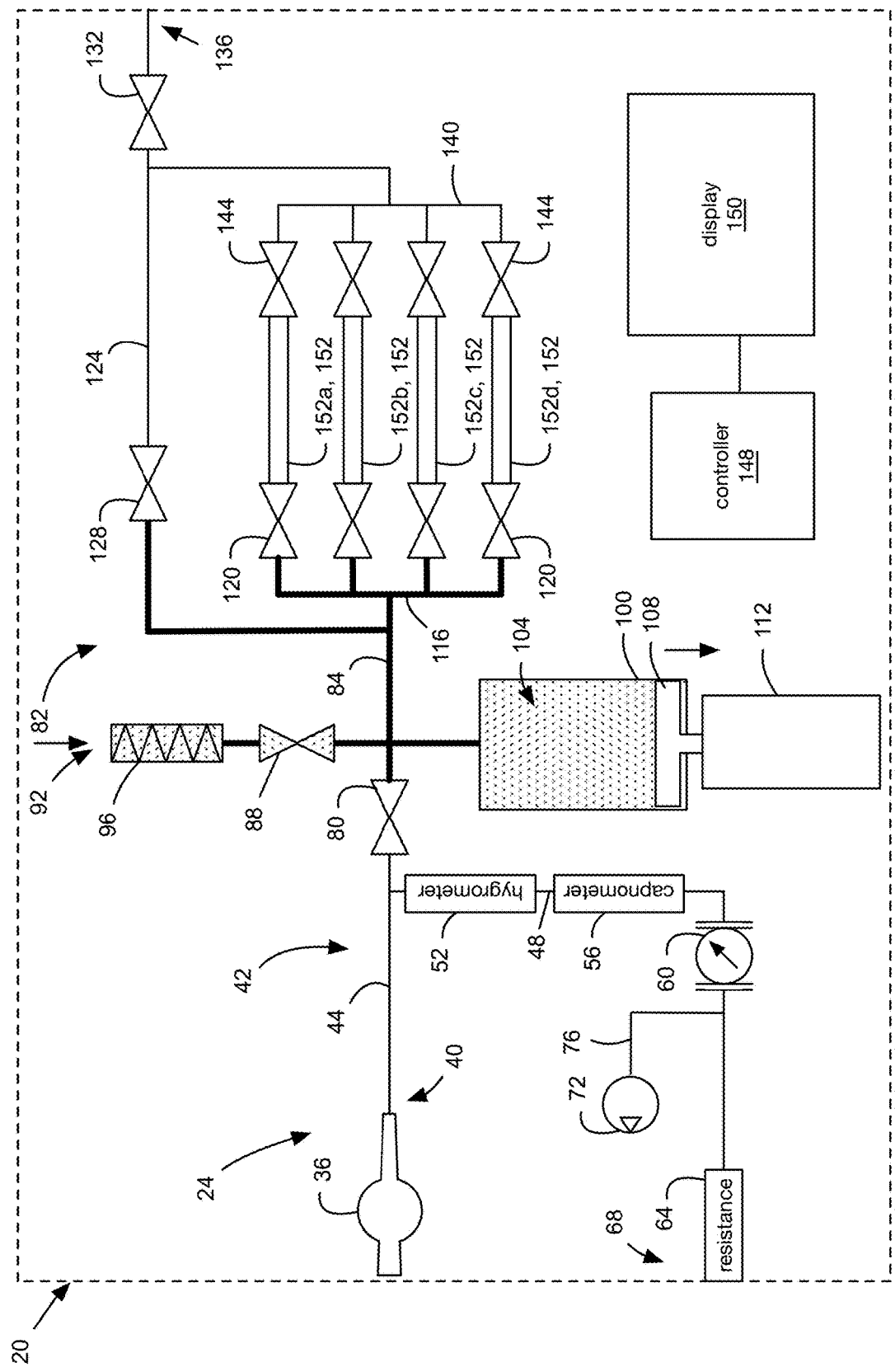
FIG. 4C shows sorbent tubes fitted in the breath sample collection apparatus of FIG. 4A and ambient air being drawn into the container.

Once the sorbent tubes are loaded, ambient air is drawn into the piston chamber 100, as is shown in FIG. 4C (214). Ambient air from the room in which the breath sample collection apparatus 20 is drawn in by controlling the piston motor 112 to actuate the piston 108. As the piston 108 is withdrawn in the piston chamber 100, the size of the cavity 104 increases and ambient air is pulled into the cavity 104 via the inlet 92, through the air filter 96 and the inlet valve 88.

Figure 4D:
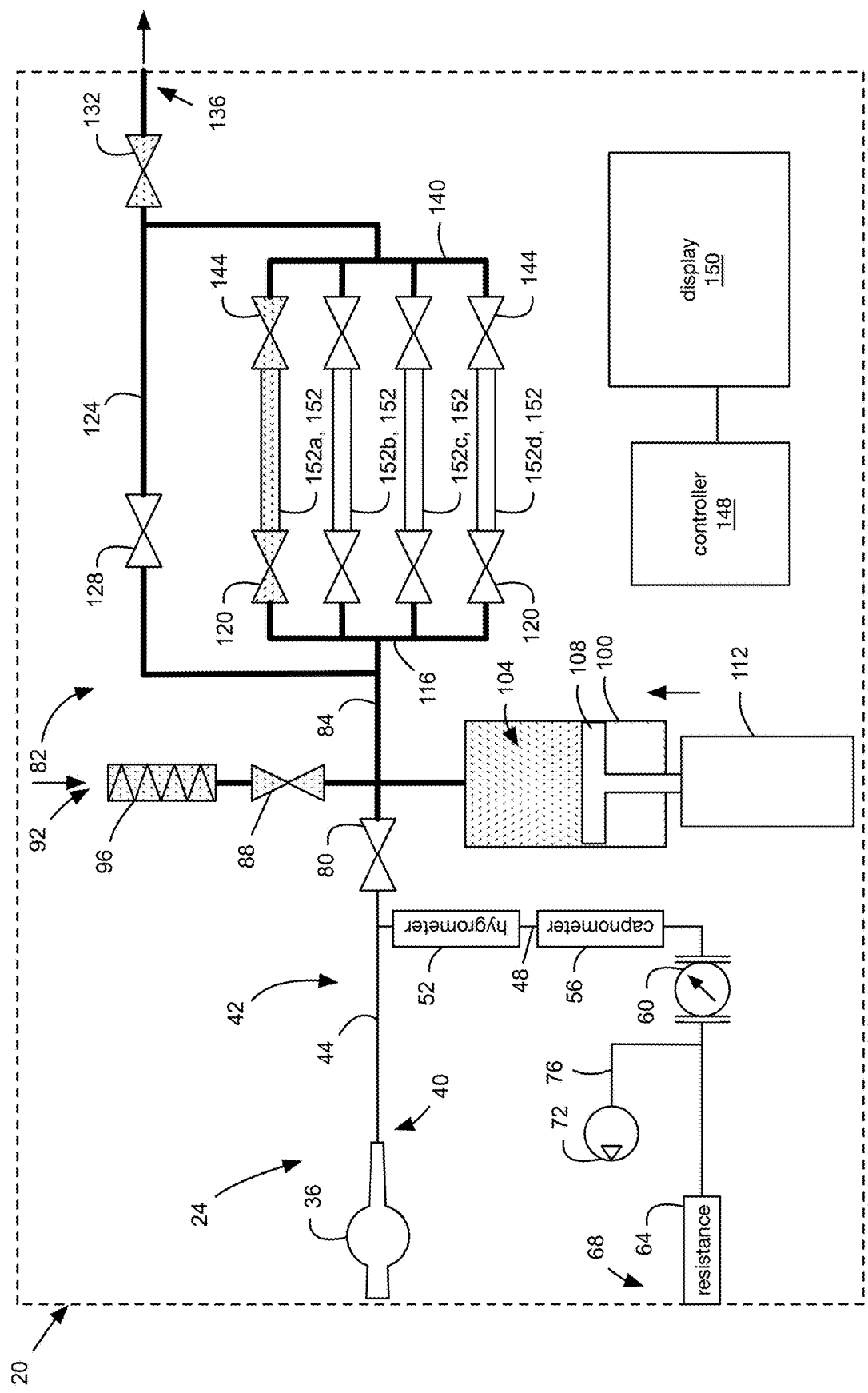
FIG. 4D shows the ambient air being impelled through one of the sorbent tubes in the breath sample collection apparatus of FIG. 4A.

Once the ambient air has been drawn into the piston chamber 100, the ambient air is flowed through a subset of the sorbent tubes 152, as shown in FIG. 4D (215). The controller 148 opens a first of the tube inlet valves 120 and a first of the tube outlet valves 144, as well as the outlet valve 132. Next, the controller 148 directs the piston motor 112 to actuate the piston 108 to move into the piston chamber 100 to decrease the volume of the cavity 104. As the cavity volume decreases, the ambient air in the cavity 104 is impelled through a first sorbent tube 152a and out through the outlet 136. The rate at which the ambient air is flowed through the sorbent tube 152a is selected to provide effective adsorption while being time-efficient.

If it is determined that a target volume of ambient air to be flowed through the sorbent tube 152a in order to capture the ambient air sample exceeds the capacity of the piston chamber (about two liters), 214 and 215 are repeated as needed until the ambient air sample has been captured in the sorbent tube 152a.

Figure 4E:
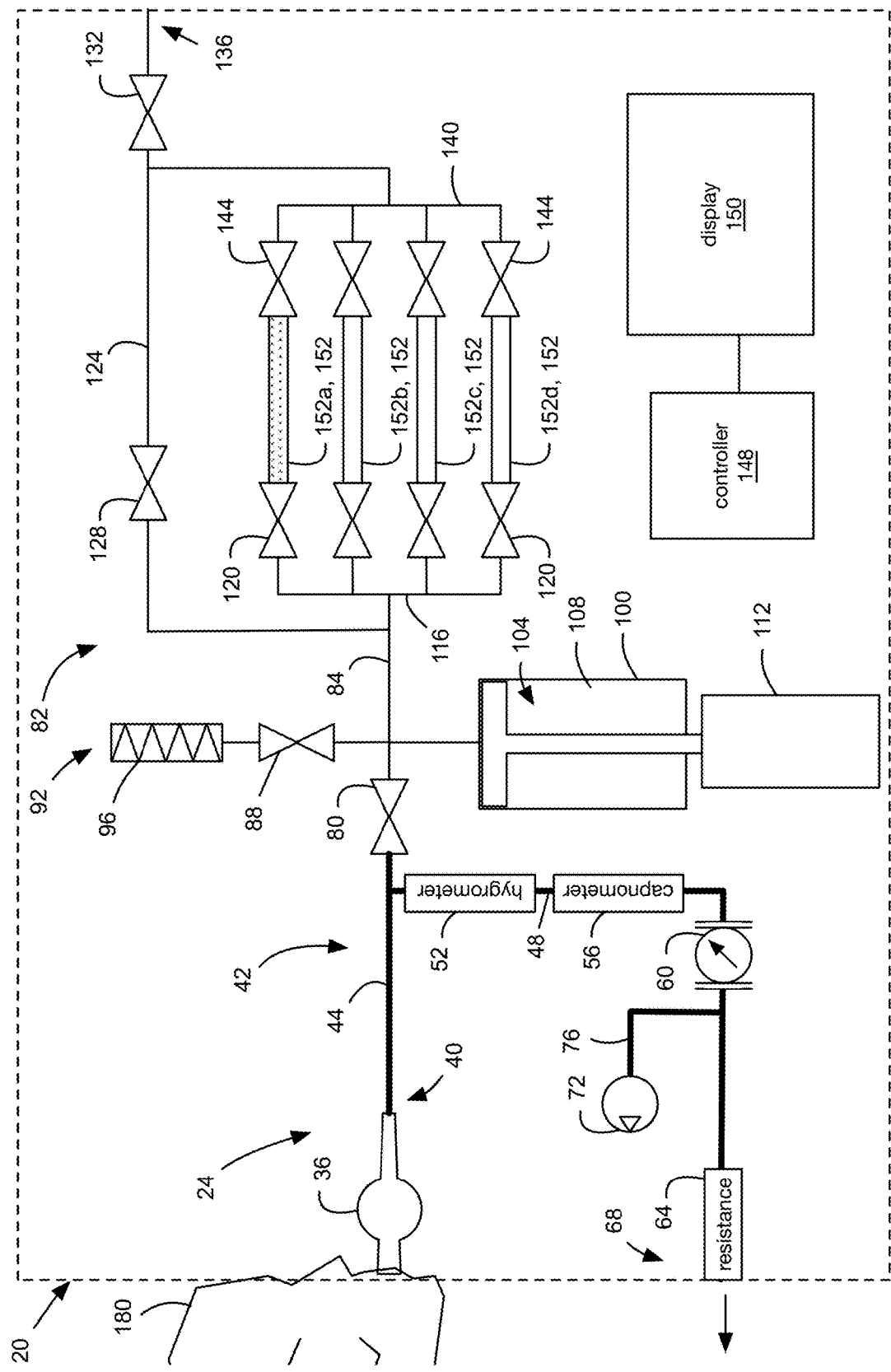
FIG. 4E shows the breath sample collection apparatus of FIG. 4A as a person commences to breathe into the breath sample collection apparatus.

Next, a person 180 from which a breath sample is being collected is directed via the display 150 to exhale into the mouthpiece 36 during a process referred to as "breath pre-collection", as is shown in FIG. 4E (216). "Breath pre-collection" is used to accustom the person 180 with the sensation of exhaling into the breath sample collection apparatus 20 in a specified manner according to criteria set out for operation of the breath sample collection apparatus 20. The display 150 presents instructions to the person 180 regarding a target exhalation rate of 20 liters per minute. By accustoming the person 180 on how to exhale into the breath sample collection apparatus 20, the person 180 typically becomes more consistent in their breaths. People typically are much better able to control their exhalation rate after performing even just one breath exhalation of training. In addition, the breath provided during the breath pre-collection phase is used to prime the conduits of the system.

As the breath collection valve 80 is closed, the breath exhaled by the person 180 travels through the breath intake conduit 44 and along the exhaust conduit 48.

During the breath pre-collection phase, the capnometer 56 is sampling the air to determine the level of carbon dioxide therein. As the capnometer 56 is sampling the air frequently, the capnometer 56 can also determine the rate of change of the level of carbon dioxide. The flow meter 60 determines the flow rate of the breath. The low-pressure resistance portion 64 provides very low flow restriction to exhalation by the person 180, and the breath exits through the exhaust conduit outlet 68.

The controller 148 constantly monitors signals from the capnometer 56 and the flow meter 60 to determine if a set of breath collection criteria are met. These breath collection criteria are (a) the carbon dioxide level reported by the capnometer 56 is within a target range defined by a minimum threshold and an infinite upper bound; (b) the rate of change of the carbon dioxide level is within a change rate target range defined by an infinite lower bound and a change rate maximum threshold; and (c) the flow rate of the breath exhalation is within a target range defined by a minimum flow rate threshold and a maximum flow rate threshold. In the present embodiment, the minimum flow rate threshold is 20 liters per minute and the maximum is 25 liters per minute. Having the flow rate of breath be within a target range provides consistency to the breath provided by the person 180. As will be understood, it can be said that the target ranges can be defined by a threshold at one of its bounds as the other bound can be logically satisfied, such as an infinite or zero bound.

The first part of the breath of the person 180 includes air from the mouth or and/or throat for which oxygen/carbon dioxide exchange did not occur in the lungs, thereby giving it a higher percentage of oxygen. As the person 180 continues to breath out, a greater portion of the breath is from the lungs where oxygen/carbon dioxide exchange occurs. As a result, the carbon dioxide released from the blood stream becomes a larger contingent (about 3-7%) of the breath. Then the carbon dioxide level hits a knee when the change rate thereof decreases dramatically. This indicates that the breath is from inside the lungs, instead of the breath from the mouth or the windpipe/trachea. This breath is referred to as alveolar breath. In the present embodiment, the target range for the carbon dioxide level is from 3% of the breath to an infinite upper bound, and the change rate target range for the carbon dioxide level is from 0% to 2% of the breath per second.

Figure 5:
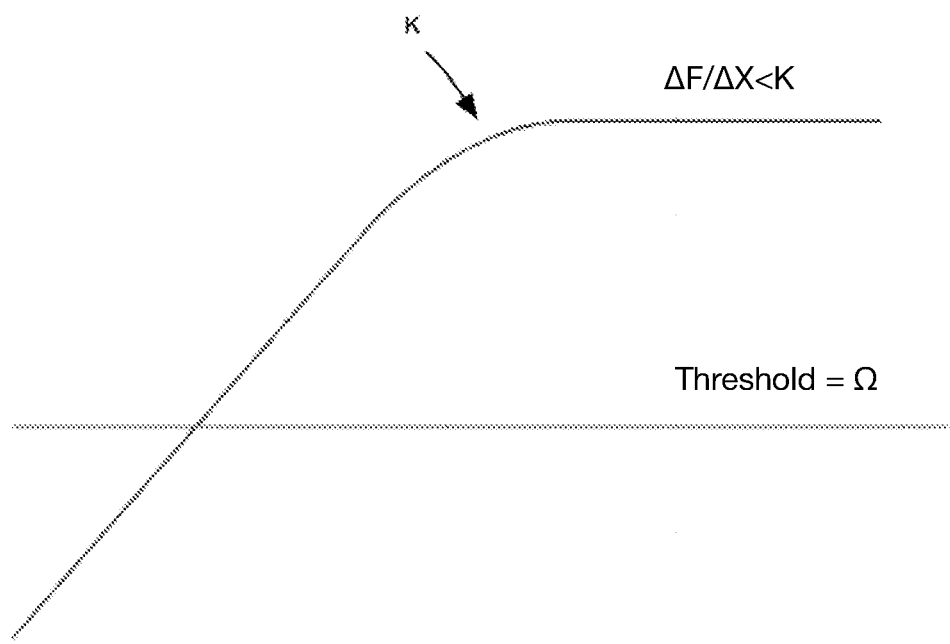
FIG. 5 shows a graph of the carbon dioxide level in breath over time during a breath.
Figure 3:
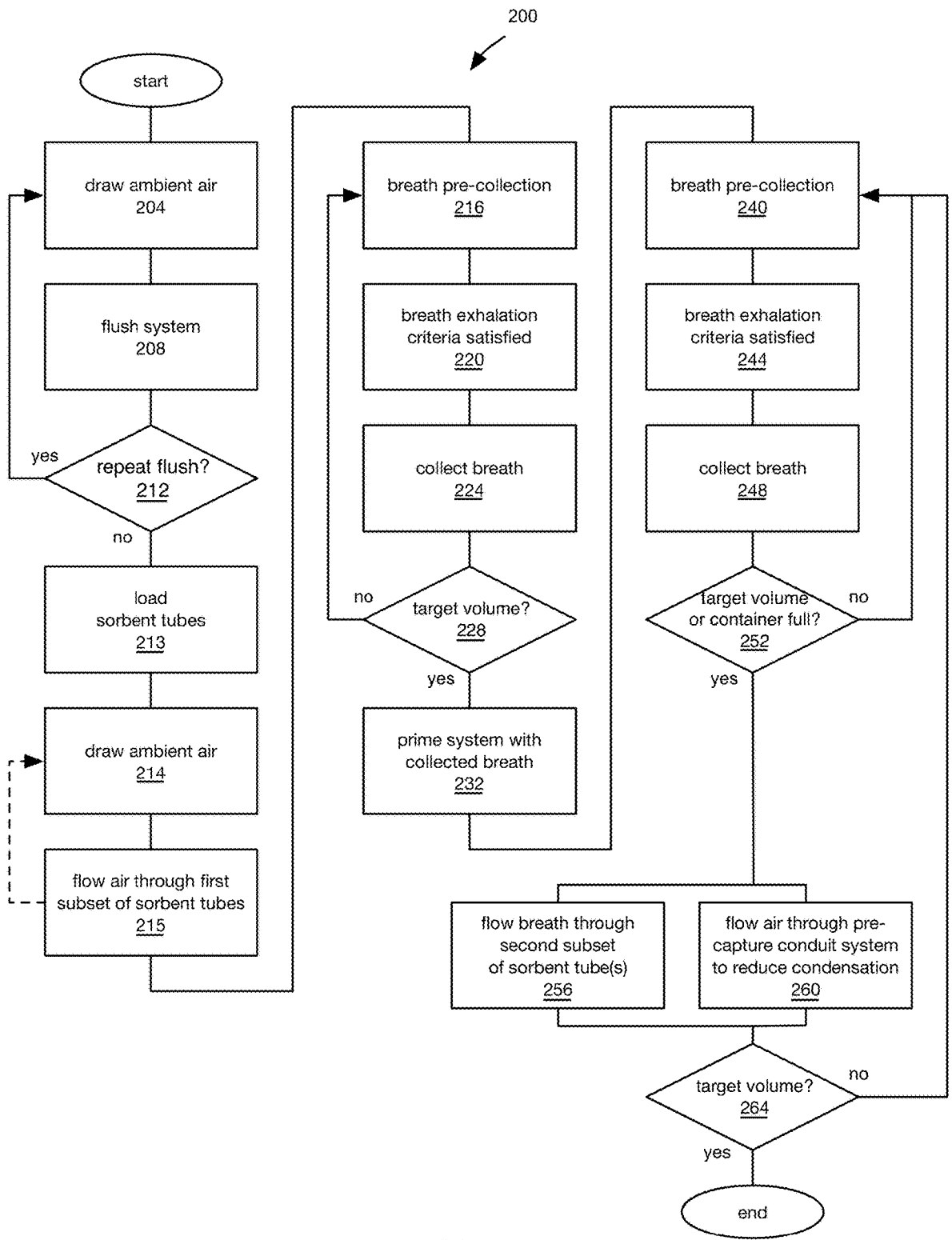
FIG. 3 is a flowchart of the general method of collecting breath using the apparatus of FIG. 1.

FIG. 5 shows the carbon dioxide level in exhaled breath over time relative to a threshold $\Omega$. The rate of change of the carbon dioxide level is generally consistently elevated until alveolar breath is being exhaled, at which point the rate of change in the carbon dioxide level drops significantly, This change of rate is reflected as a knee K. Thereafter, the carbon dioxide level in the exhaled alveolar breath is stable.

In the present configuration, the breath collection criteria are as follows. The carbon dioxide level is above a threshold of 2%. This level is well above atmospheric levels, but below what is expected to be seen in a person (e.g., 3% is lowest from people with poor lung function). The rate of change of the carbon dioxide level is below a specified threshold. Further, the flow rate of the breath exhalation exceeds 20 liters per minute.

The three criteria prevent the trigger of breath collection during less-than-ideal circumstances in many cases.

Figure 4F:
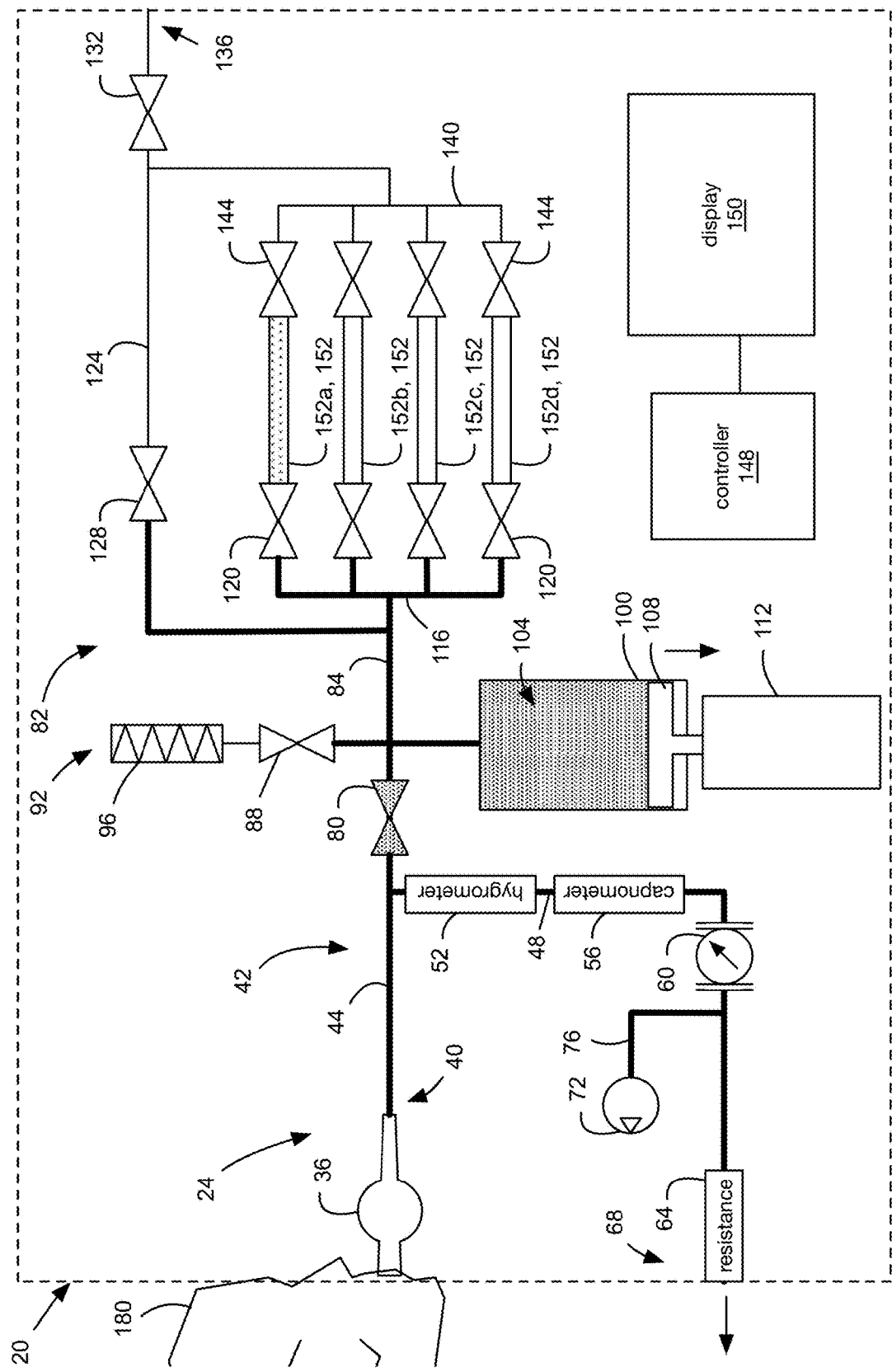
FIG. 4F shows the breath sample collection apparatus of FIG. 4C collecting a breath sample after the breath is determined to be alveolar.

Upon the satisfaction of all three criteria, breath collection commences as is illustrated in FIG. 4F (224). Once the three criteria are satisfied, the controller 148 opens the breath collection valve 80 and directs the piston motor 112 to drive the piston 108 to increase the volume of the cavity 104 as the breath is being received. The piston 108 is controlled to actuate at a rate dependent upon the flow rate reported by the flow meter 60 to provide a volume increase rate for the cavity 104. In this particular embodiment, the volume increase rate of the cavity 104 achieved as a result of actuating the piston 108 is proportional to the flow rate detected by the flow meter 60 along the exhaust conduit 48. In other embodiments, the volume change rate of the cavity 104 can be changed in a different manner as a function of the flow rate reported by the flow meter 60.

As the volume of the cavity 104 increases, it is easier for the person 180 to exhale due to the pressure differential created. If the person 180 is exhaling at 20 liters per minute, the person 180 is only breathing out with force required for four liters per minute as 16 liters per minute are being pulled out by the pressure differential in the system as a result of the increasing volume of the cavity 104. This can enable people with reduced ability to exhale with force to provide a breath sample, such as can be the case with lung cancer and respiratory conditions.

As previously indicated, the flow meter 60 is positioned along a normally downstream path for airflow to inhibit the contamination of a presently collected breath sample with breath from a previous breath sample provider that adhered to the flow meter 60. If the actuation rate of the piston 108, and thus the increase rate of the cavity volume, were fixed, more or less of the breath would be expelled via the flow meter 60 when the person 180 exhaled more rapidly. This can result in a more-than-desired amount of the exhaled breath escaping along the exhaust conduit 48, and issues when the flow rate drops below the volume increase rate of the cavity 104.

In the present configuration, the controller 148 controls the piston 108 to increase the volume of the cavity 104 at a rate that is dependent on the flow rate measured by the flow meter 60. In particular, the volume of the cavity 104 is increased at four times the flow rate measured by the flow meter 60. That is, the increase in volume of the cavity 104 captures 80% of the breath received from the person 180.

The hygrometer 52, the capnometer 56, and the flow meter 60 are all positioned along the exhaust conduit 48, away from the breath intake conduit 44. These metering devices can off-gas VOCs. Further, these metering devices can become contaminated by the breath of a person from which breath was previously collected. By placing these metering devices along the exhaust conduit 48, along which breath flows away from the direct path along the breath intake conduit 44, contamination by the other breath or off-gassed VOCs is inhibited. Further, these metering devices and the conduits are provided with an inert internal coating to reduce the probability that breath or off-gassed VOCs adhere to their internal surfaces to thereby further reduce the probability of contamination of a breath sample by the previously received breath and off-gassed VOCs.

By allowing some of the breath received to travel along the exhaust conduit 48 along which the hygrometer 52, the capnometer 56, and the flow meter 60 are located, the overall generally unrestricted breath exhalation rate can be determined. This breath exhalation rate is equal to the flow rate measured by the flow meter 60 plus the rate of increase of the volume of the cavity 104 determined based on the actuation rate of the position of the piston 108. This breath exhalation rate can then be used to determine how fast to increase the volume of the cavity 104. By keeping the rate of increase of the volume of the cavity 104 below the determined breath exhalation rate, some of the breath will always travel down the exhaust conduit 48 to enable continued monitoring of the overall breath exhalation rate.

This ratio of 80% of the overall breath exhalation rate has been selected to afford a reaction time buffer so that if the exhalation rate of the person quickly drops off, the volume increase rate of the cavity 104 can be adjusted with a minor amount of lag with very little chance of exceeding the breath exhalation rate. If the volume increase rate of the cavity 104 exceeds the breath exhalation rate of the person, the pressure differential in the system may draw breath from the person unnaturally, which can be an undesirable outcome, and can draw in ambient air through the exhaust conduit outlet 68.

Information regarding the overall exhalation rate is presented to the person 180 on the display 150 to encourage the person 180 to exhale within the target range or at least at the threshold rate.

If the person 180 increases their exhalation rate, up to a threshold 25 liters per minute, the piston 108 is actuated by the controller to move to cause the cavity 104 to increase in volume so that 80% of the exhaled breath is collected within the cavity 104.

If the person 180 reduces their exhalation rate, the piston speed is adjusted so that the change in volume of the cavity 104 is always below the rate of exhalation to ensure that no air is pulled in via the flow meter route and that the flow rate of breath can be metered via the flow meter 60.

If the flow rate detected by the flow meter 60 falls within a flow rate termination range, movement of the piston 108 is stopped to stop the collection of breath in the piston chamber 100. The flow rate termination range in the present embodiment is from an infinite lower bound to two liters of breath per minute.

The person 180 may not have enough breath to fill the entire piston chamber 100. Accordingly, once the flow meter 60 reports that the exhalation rate drops below a certain value, movement of the piston 108, and thus breath collection, is stopped.

The controller 148 then determines if a target volume has been collected to prime the system (228). The breath sample collection apparatus 20 collects one liter of breath to prime the system. If less than the target volume of one liter of breath has been collected, the controller 147 controls the breath sample collection apparatus 20 to perform breath pre-collection at 216.

Figure 4G:
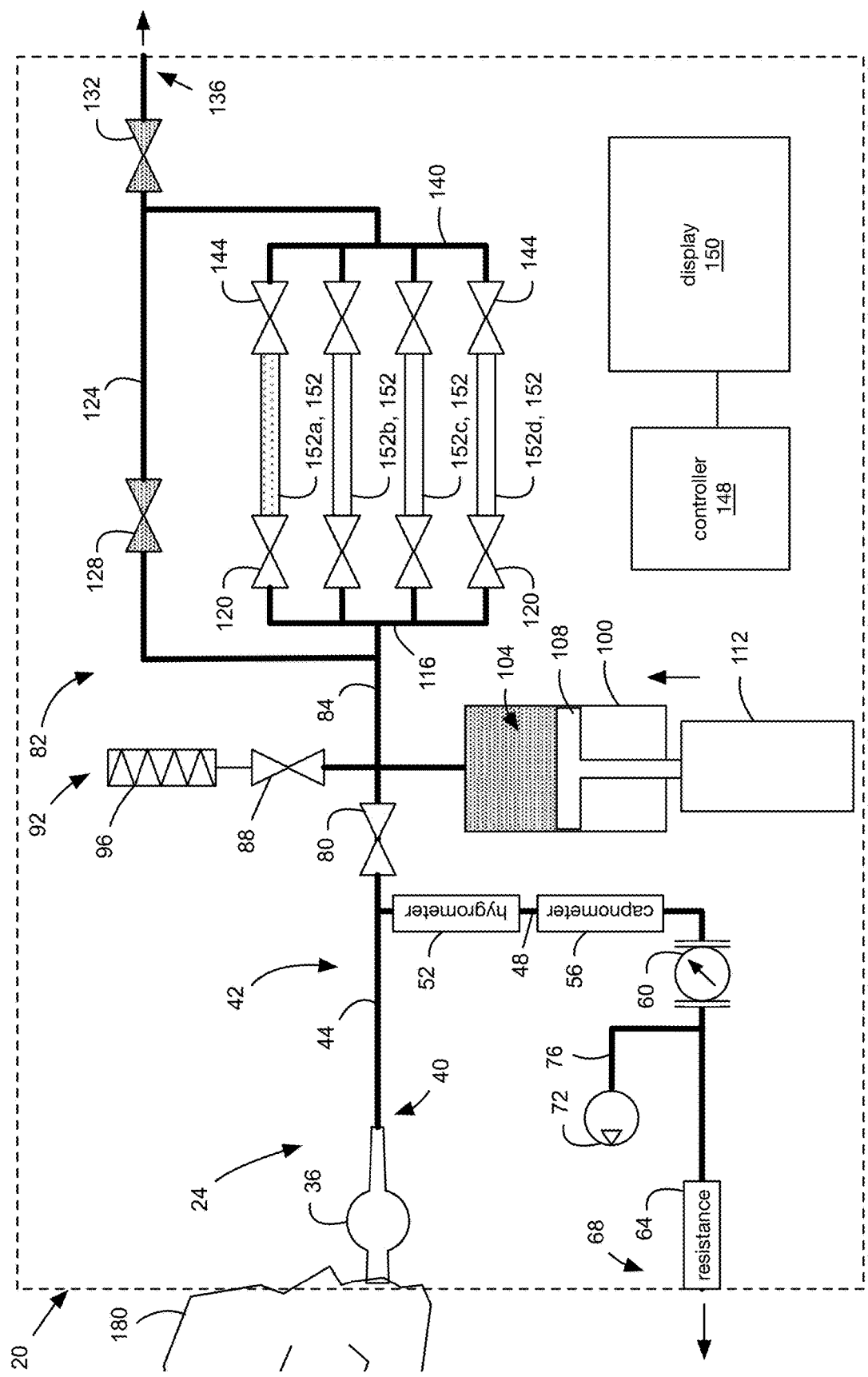
FIG. 4G shows the breath sample collection apparatus of FIG. 4C being used to prime the breath sample collection apparatus.

If, instead, it is determined at 228 that sufficient breath has been collected to prime the system, the collected breath is used to prime the system, as is shown in FIG. 4G (232). The controller 184 directs the breath collection valve 80 to close, and the bypass valve 128 and the outlet valve 132 to open. Further, the piston motor 112 is directed to drive the piston 108 into the piston chamber 100, thereby reducing the volume of the cavity 104. As the volume of the cavity 104 is reduced (i.e., the volume decrease rate), the breath contained therein is impelled through the breath collection conduit 84, the tube inlet manifold 116, the tube outlet manifold 140, the bypass conduit 124, and out the outlet 136. This primes these conduits with the collected breath of the person 180.

Figure 4H:
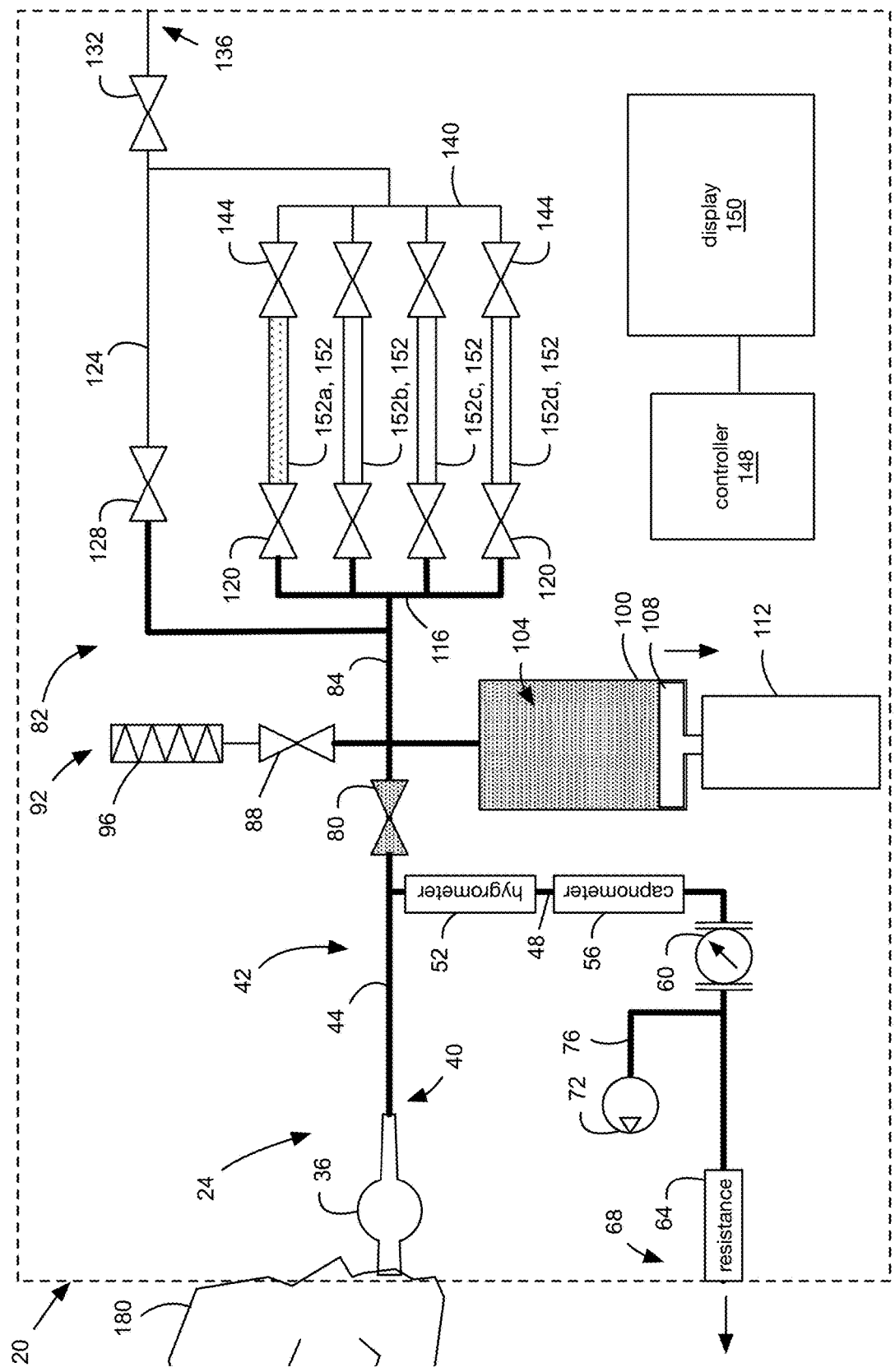
FIG. 4H shows the breath sample collection apparatus of FIG. 4C collecting a breath sample after sorbent tubes have been loaded.

Upon priming the capture conduit system 82, breath is collected again using the same general approach at 216 to 228. That is, breath pre-collection is performed again (240). During breath pre-collection, the controller 148 determines if the breath exhalation criteria are satisfied (244). If they are, breath is collected as is shown in FIG. 4H (248).

Then it is determined if a target volume of breath for adsorbing has been collected or if the piston chamber 100 is full (252). If the target volume of breath for adsorbing in the sorbent tube(s) 152 has not yet been collected and if the piston chamber 100 is not full, more breath is collected again starting with breath pre-collection at 240. The person 180 is instructed to take another breath.

Figure 4I:
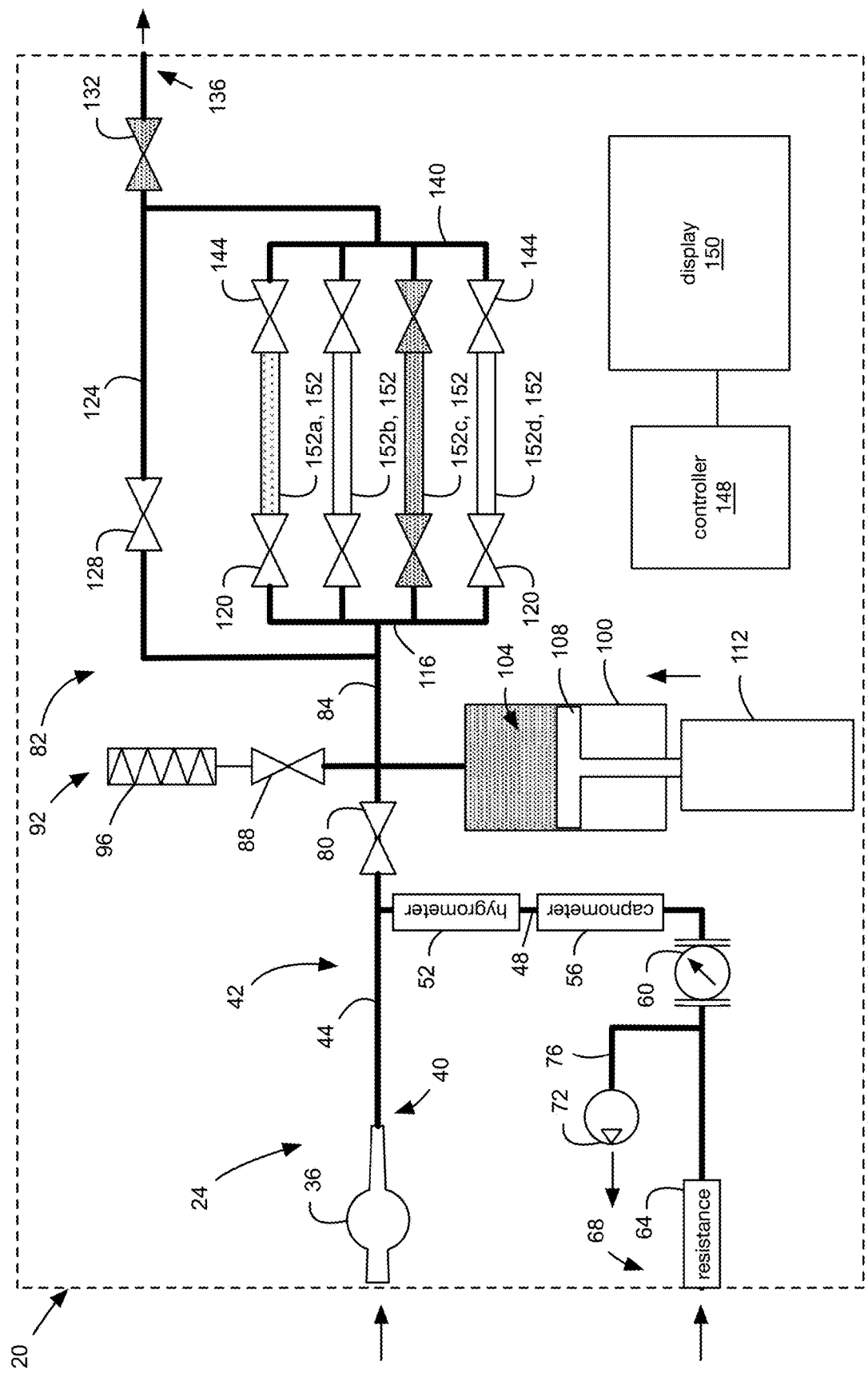
FIG. 4I shows the breath sample collection apparatus of FIG. 4C flowing the collected breath sample through one of the sorbent tubes.

If, instead, it is determined that the target volume of breath has been collected or that the piston chamber 100 is full at 252, the breath is flowed through a second subset of the sorbent tubes 152 (256). FIG. 4I illustrates the piston chamber 100 having been filled with breath. The controller 148 is configured to control a flow of the at least some of the breath from the container to a subset of the sorbent tubes 152 asynchronous of when the exhaled breath is received. That is, the flowing of breath from the container to a subset of the sorbent tubes 152 can be performed independent of when the exhaled breath is received, apart from having to occur after receiving the exhaled breath. The second subset can be any number of the sorbent tubes 152 connected to the breath sample collection apparatus 20 that have not been adsorbed with ambient air. Once the machine has collected a full piston chamber 100 of breath after priming the conduits, the controller 148 closes the breath collection valve 80, and controls each of the tube inlet valves 120, either leaving the tube inlet valves 120 in their previously closed or open state or opening or closing each of the tube inlet valves 120, to select a subset of the sorbent tubes 152 through which the at least some of the breath is flowed through. In this embodiment, the controller 148 opens a corresponding one of the tube inlet valves 120 and the tube outlet valves 144 for a sorbent tube 152 in which the sample is to be adsorbed, as well as the outlet valve 132. The piston 108 is controlled by the controller 148 to slowly move to push the breath therein through the selected sorbent tube 152 at a predetermined rate pushing breath through the designated sorbent tube 152.

As the breath is being flowed through the second subset of sorbent tubes 152, air is simultaneously flowed through the pre-collection conduit system 46 to reduce condensation therein (260). In particular, the controller 148 controls the pump 72 to turn on to draw ambient air from the mouthpiece 36 and the exhaust conduit outlet 68 and through the exhaust conduit 48 to help relieve condensation out of the line. As the measurement equipment does not work optimally in very humid conditions, the pump 72 acts to lower condensation/humidity in the exhaust conduit 48. As the pump 72 is operated, the humidity level is monitored via the hygrometer 52.

Figure 6:
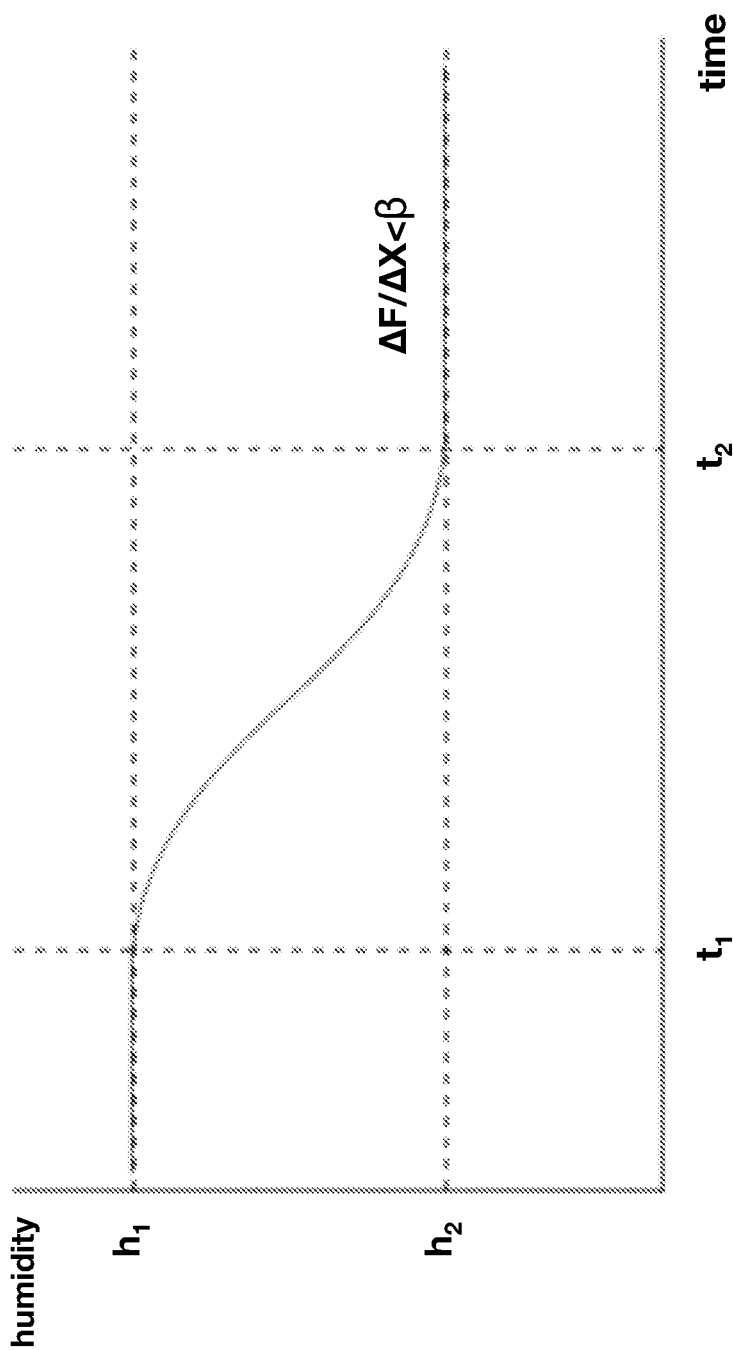
FIG. 6 shows the humidity level in the breath sample collection apparatus while the humidity is being removed by the pump.

FIG. 6 shows a typical graph of humidity level detected by the hygrometer 52 over time. Before the pump 72 is turned on at $t_1$, the humidity is at a first level $h_1$. High levels of condensation can be observed in the clear mouthpiece 36. After the pump 72 is turned on, the change rate in the humidity level is negative as the humidity level drops over time. When the change rate of the humidity level is within a change rate target range at time $t_2$, the controller 148 terminates operation of the pump 72, as it is deemed that the pre-collection conduit system 46 is relatively free of condensation and that continued operation of the pump 72 has relatively little value. This humidity level change rate target range in the present embodiment is −0.05% relative humidity per second to 0% relative humidity per second, but can be varied in other scenarios. In this manner, the breath sample collection apparatus 20 can perform maintenance during otherwise idle time. In other embodiments, this condensation reduction phase can be run based on a humidity level being outside of a humidity level target range of values from zero to the humidity level of the ambient air via use of a secondary external hygrometer.

The rate at which the breath is flowed through the sorbent tube 152 is 500 milliliters per minute. It has been found that the break-through volume for the sorbent tube 152 is affected by the adsorb flow rate. The break-through volume is the volume at which half of the sample is captured by a sorbent tube 152 and the other half flows through to the other side of the sorbent tube 152. At the break-through volume, the adsorbent in the sorbent tube 152 is at the point where enough surface is used so that it is just as easy for molecules to go through as it is for molecules to be trapped. Increasing the flow rate of breath through a sorbent tube 152 decreases the break-through volume. This skews the captured sample to the heavier molecules and less of the smaller molecules. By controlling the flow rate of the breath through the sorbent tubes 152, the adsorption rate for certain molecules can be controlled.

It is then determined if a target volume has been flowed through the subset of sorbent tubes 152 (264). If a desired amount of breath has not yet been flowed through the subset of sorbent tubes 152, the method 200 returns to 240, at which more breath is collected for flowing through the subset of the sorbent tubes 152.

Upon determining that a target volume has been flowed through the currently selected sorbent tube 152, the controller 148 can terminate flowing the breath through the sorbent tube 152 via the tube inlet and outlet valves 120, 144 and commence flowing the breath through another of the sorbent tubes 152.

The breath sample collection apparatus 20 can be configured to select different sized subsets of the sorbent tubes for ambient air and breath samples. In one preferred embodiment, two sorbent tubes of ambient air samples and two sorbent tubes of breath samples are collected. In other embodiments, no ambient air may be collected.

While not explicitly illustrated, it will be understood that the controller 148 is connected to each of the valves, the hygrometer 52, the capnometer 56, the flow meter 60, the pump 72, the piston motor 112, as well as other components of the breath sample collection apparatus 20.

In other embodiments, the container with a controllable volume can be any other structure for providing a cavity with a controllable volume. For example, in one particular embodiment, the container can include a bellows-like structure.

Figure 7A:
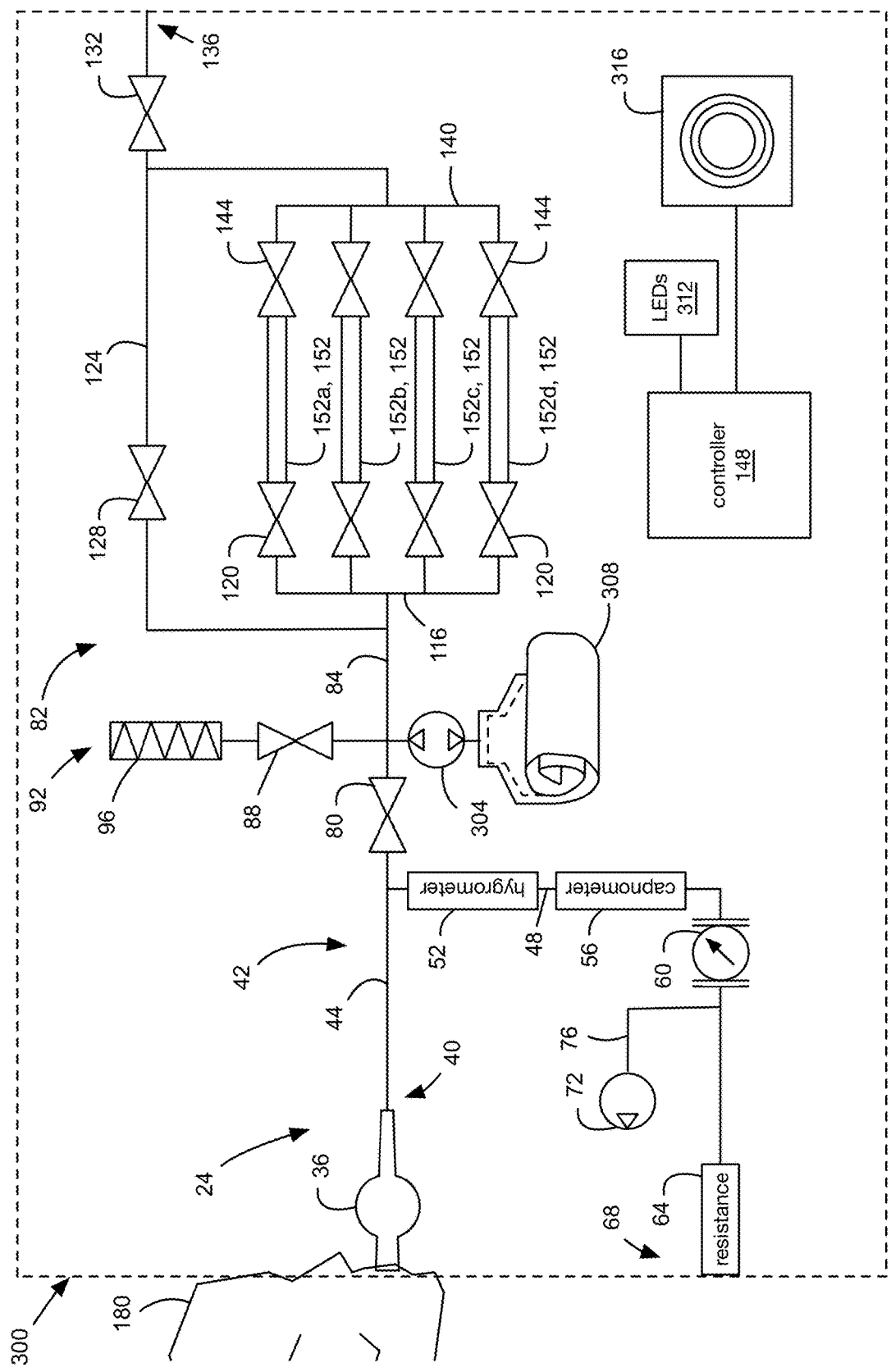
FIG. 7A shows an apparatus for collecting a breath sample including a collapsed bag and its operating environment in accordance with another embodiment.

FIG. 7A shows a breath sample collection apparatus 300 in accordance with another embodiment. The breath sample collection apparatus 300 is similar to the breath sample collection apparatus 20 of FIGS. 1 and 4A to 41, except that the breath sample collection apparatus 300 employs a two-way pump 304 and a container that includes an at least partially flexible collapsible receptacle 308 in place of the piston chamber 100 and piston 108. The at least partially flexible collapsible receptacle 308 is secured to the two-way pump 304 that is, in turn, secured to the breath collection conduit 84.

In this embodiment, the at least partially flexible collapsible receptacle 308 is a bag made of polyvinyl fluoride, a highly flexible material that has high tensile characteristics. While not impermeable, It has a suitably low permeability that, for this application, does not impact its performance significantly. Further, it is relatively inert. Other suitably flexible, relatively non-porous, and relatively inert materials can additionally or alternatively be used in other embodiments. Further, the receptacle can also include inflexible portions.

The at least partially flexible collapsible receptacle 308 has an interior cavity that has a volume defined by the amount of a fluid therein. In FIG. 7A, the at least partially flexible collapsible receptacle 308 is shown having substantially no breath or ambient air therein, and thus the cavity has substantially no volume. In this collapsed state, the at least partially flexible collapsible receptacle 308 can be compacted to facilitate packing.

The two-way pump 304 has a controllable flow rate and flows breath and/or ambient air in both directions. It is controllable by the controller 148 to draw breath and/or ambient air from the breath collection conduit system 82 into the at least partially flexible collapsible receptacle 308, and draws breath and/or ambient air from the at least partially flexible collapsible receptacle 308 into the breath collection conduit system 82. Thus, the controller 148 can control the two-way pump 304 and, as a result, the at least partially flexible collapsible receptacle 308 to provide the same general functionality as the piston chamber 100, the piston motor 112, and the piston 108. That is, the controller 148 can, through operation of the pump, control the volume of the at least partially flexible collapsible receptacle 308.

Figure 7B:
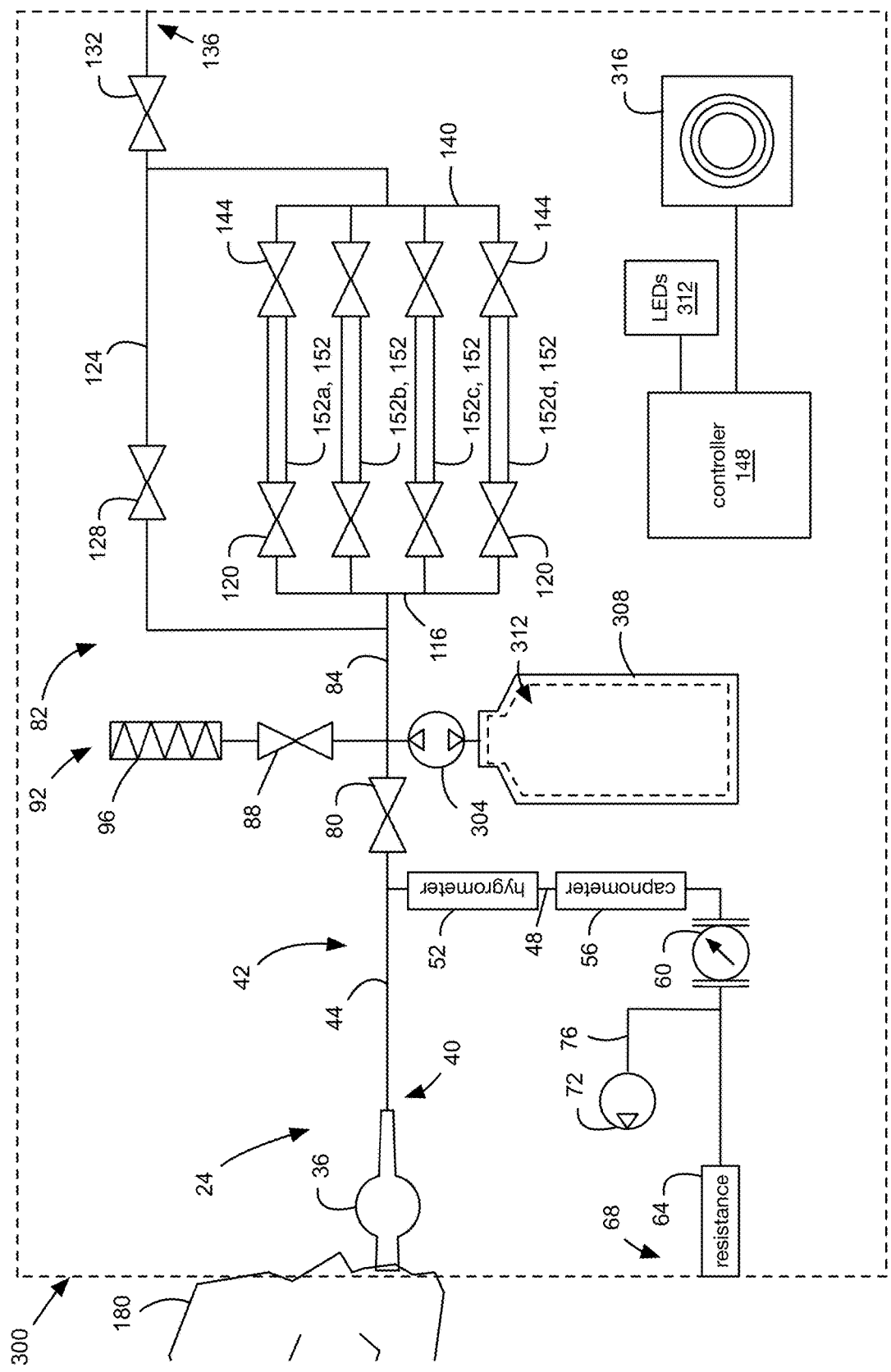
FIG. 7B shows the apparatus of FIG. 7A, wherein the bag is expanded.

FIG. 7B shows the at least partially flexible collapsible receptacle 308 after the two-way pump 304 has drawn breath and/or ambient air therein, thus enlarging the cavity of the at least partially flexible collapsible receptacle 308 and the at least partially flexible collapsible receptacle 308 itself.

The breath sample collection apparatus 300 also differs in that it has an array of light elements in the form of LEDs 312 and an audio speaker 316 in place of a display. Flow rate notifications can be presented to a user via the LEDs 312. For example, the array of LEDs 312 can include a sequence of a red LED, a yellow LED, a green LED, a yellow LED, and a red LED. When the flow rate of breath through the breath input interface 24 is too low, a corresponding red or yellow LED can be illuminated. If the flow rate of breath through the breath input interface 24 is satisfactory, the green LED can be illuminated. Similarly, when the flow rate of breath through the breath input interface 24 is too high, a corresponding second red or yellow LED can be illuminated. In this manner, a person can be shown visually how his breath flow rate compares to a target flow rate. In other embodiments, other types of light elements can be employed.

The audio speaker 316 can be used in a similar manner, with flow rate notifications being provided by means of clicks of different frequencies, sounds of different frequencies, different sounds, etc.

Figure 8:
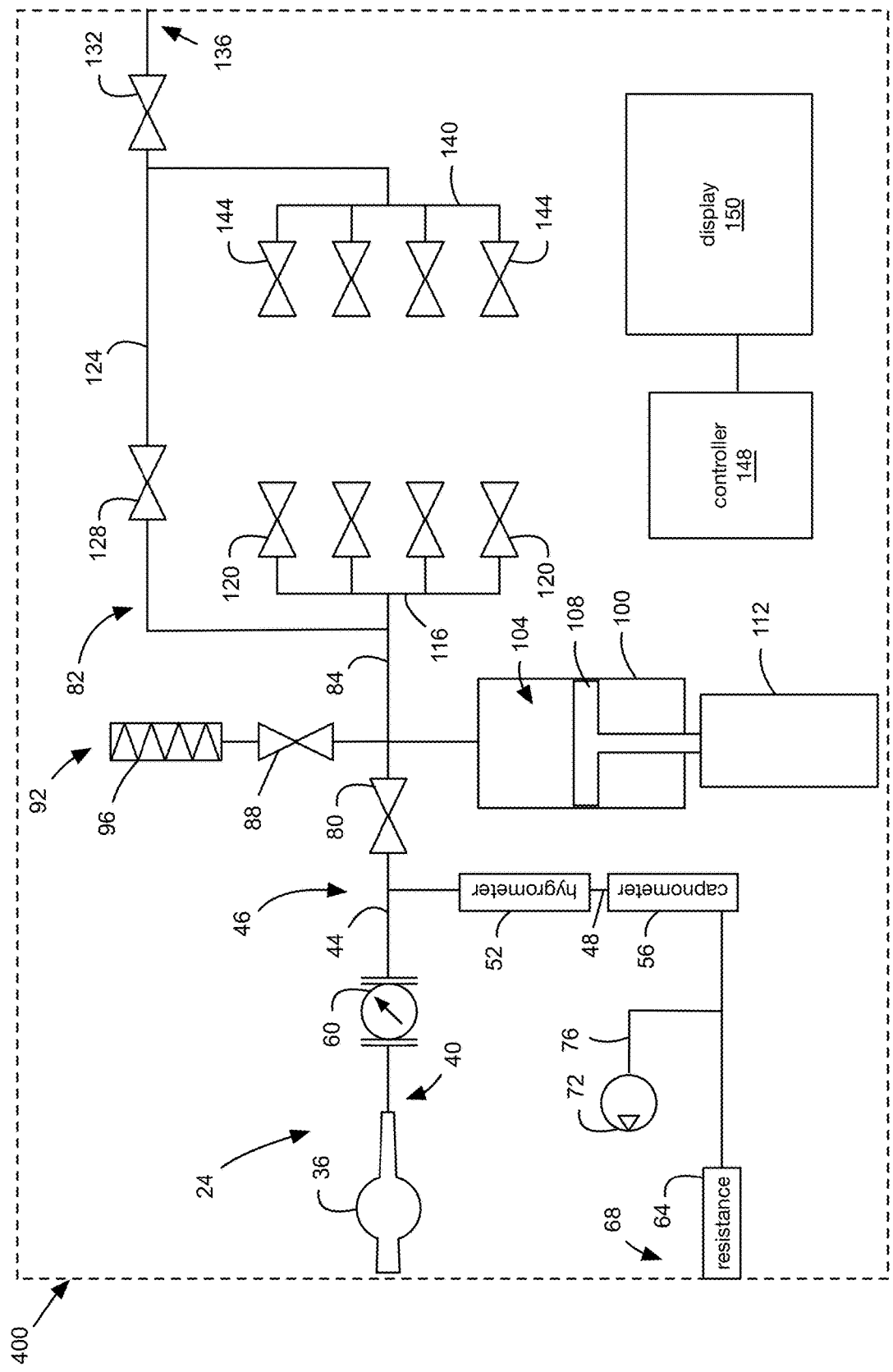
FIG. 8 shows a breath sample collection apparatus in accordance with a further embodiment.

FIG. 8 shows a breath sample collection apparatus 400 in accordance with a further embodiment. In this embodiment, the flow meter 60 is positioned along the breath intake conduit 44. Thus, the flow meter 60 measures the full exhaled breath rate along the breath intake conduit 44. During breath collection, the controller 148 can control the piston motor 112 to actuate the piston 108 so that the volume change rate of the cavity 104 is set to a proportion of the flow rate measured by the flow meter 60. In a preferred embodiment, the volume change rate of the cavity 104 is set to 80% of the flow rate measured by the flow meter 60 during breath collection. The excess breath flows along the exhaust conduit 48 and out the exhaust conduit outlet 68.

While, in the above-described embodiments, a capnometer is employed to measure the level of carbon dioxide in the breath, in other embodiments, other types of metering devices can be employed for measuring the levels of other constituents in the breath, such as those that can indicate when alveolar breath is being detected. These metering devices can detect levels and change rates in these levels of these other constituents to determine when alveolar breath is being detected. For example, a metering device can measure an oxygen level in the breath and, upon detecting that the change in the oxygen level has fallen within a change rate target range having a change rate maximum threshold, it can be determined that alveolar breath is now being detected.

In other embodiments, other types of breath sample storage devices apart from sorbent tubes can be employed. For example, solid-phase microextraction ("SPME") fibres can be alternatively used to store the breath sample. Another example is silica gel. Still other examples are powders that produce a chemical reaction resulting in a visible indication (e.g., Drierite turns purple in the presence of humidity) or a by-product chemical that can be more easily analyzed later. Other types of breath sample storage devices will occur to those skilled in the art.

The volume of the container can be mechanically controlled in other manners. In one particular embodiment, the container can include a bellows that can be actuated to expand and contract.

Although specific advantages have been enumerated above, various embodiments may include some, none, or all of the enumerated advantages.

Persons skilled in the art will appreciate that there are yet more alternative implementations and modifications possible, and that the above examples are only illustrations of one or more implementations. The scope, therefore, is only to be limited by the claims appended hereto.

LIST OF REFERENCE NUMERALS 20 breath sample collection apparatus
24 breath input interface
36 mouthpiece
40 breath intake end
44 breath intake conduit
46 pre-collection conduit system
48 exhaust conduit
52 hygrometer
56 capnometer
60 flow meter
64 low-pressure resistance portion
68 exhaust conduit outlet
72 pump
76 pump conduit
80 breath collection valve
82 capture conduit system
84 breath collection conduit
88 intake valve
92 ambient air inlet
96 air filter
100 piston chamber
104 cavity
108 piston
112 piston motor
116 tube inlet manifold
120 tube inlet valve
124 bypass conduit
128 bypass valve
132 outlet valve
136 outlet
140 tube outlet manifold
144 tube outlet valve
148 controller
150 display
152 sorbent tube
156 stainless-steel casing
160 aperture
164 receiving end
168 foam separator
172 adsorbent material
176 foam separator
180 person
200 method
204 draw ambient air
208 flush system
212 repeat flush?
213 load sorbent tubes
214 draw ambient air
215 flow air through first subset of sorbent tubes
216 breath pre-collection
220 breath exhalation criteria satisfied?
224 breath collected to prime system
228 target volume?
232 prime system with collected breath
236 load sorbent tubes
240 breath pre-collection
244 breath exhalation criteria satisfied
248 collect breath
252 target volume or full container?
256 flow breath through sorbent tube(s)
260 flow air through pre-capture conduit system to reduce condensation
264 target volume?
300 breath sample collection apparatus
304 two-way pump
308 flexible collapsible receptacle
312 LEDs
316 speaker

What is claimed is:

1. An apparatus for collecting a breath sample, comprising:
a breath input interface configured to receive exhaled breath;
a container connected to the breath input interface for receiving at least some of the exhaled breath, the container having a cavity with a volume that is controllable;
a breath intake conduit of a first conduit system extending from the breath input interface and towards the container, an exhaust conduit of the first conduit system branching from the breath collecting portion at a first end thereof and having an outlet at a second end thereof;
a hygrometer positioned between the breath input interface and the outlet to measure a humidity level;
a pump positioned between the breath input interface and the outlet to draw in air from the breath input interface expel the air via the outlet; and
at least one controller configured to activate the pump, based on the humidity level measured by the hygrometer, to reduce humidity in the breath input interface and along the breath intake conduit and the exhaust conduit.

2. The apparatus of claim 1, wherein the volume of the container is directly mechanically controllable by the at least one controller.

3. The apparatus of claim 2, wherein the container comprises a piston chamber having an actuatable piston positioned therein, a position of the piston in the piston chamber defining the volume of a cavity.

4. The apparatus of claim 3, further comprising a valve positioned to control travel of the exhaled breath to the piston chamber.

5. The apparatus of claim 4, further comprising at least one sorbent tube connected to the container, wherein the at least one controller is configured to control the valve to close and control actuation of the piston to impel the breath in the cavity through the at least one sorbent tube.

6. The apparatus of claim 1, wherein the container includes an at least partially flexible collapsible receptacle, and wherein the apparatus further comprises a pump configured intermediate the breath input interface and the container to impel the breath into the at least partially flexible collapsible receptacle at a volume increase rate.

7. The apparatus of claim 6, further comprising at least one sorbent tube connected to the at least partially flexible collapsible receptacle, wherein the at least one controller is configured to control the pump to impel the breath in the cavity through a subset of the at least one sorbent tube.

8. The apparatus of claim 7, further comprising a valve positioned to control travel of the exhaled breath to a piston chamber.

9. The apparatus of claim 1, further comprising a valve positioned to control travel of the exhaled breath to a piston chamber.

10. The apparatus of claim 9, further comprising a metering device positioned to determine a constituent level in the exhaust conduit, and wherein the at least one controller is configured to determine if the constituent level is within a constituent level target range, determine if a change rate in the constituent level is within a constituent level change rate target range, and control the valve to open at least partially based on whether the constituent level is within the constituent level target range and the change rate is within the constituent level change rate target range.

11. The apparatus of claim 10, wherein the metering device is a capnometer, the constituent level is a carbon dioxide level, the constituent level target range is a carbon dioxide level target range, and the constituent level change rate target range is a carbon dioxide level change rate target range.

12. The apparatus of claim 1, further comprising:
a breath intake conduit of a first conduit system extending from the breath input interface and towards the container; and
a flow meter positioned to measure a flow rate of the exhaled breath along the breath intake conduit.

13. The apparatus of claim 12, wherein a volume increase rate of the volume of the container is proportional to the flow rate along the breath intake conduit.

14. The apparatus of claim 13, wherein the volume of the container is directly mechanically controllable by the at least one controller.

15. The apparatus of claim 14, wherein the container comprises a piston chamber having an actuatable piston positioned therein, a position of the piston in the piston chamber defining the volume of a cavity.

16. The apparatus of claim 15, further comprising a valve positioned to control travel of the exhaled breath to the piston chamber.

17. The apparatus of claim 16, further comprising at least one sorbent tube connected to the container, wherein the at least one controller is configured to control the valve to close and control actuation of the piston to impel the breath in the cavity through a subset of the at least one sorbent tube.

18. The apparatus of claim 13, wherein the container includes an at least partially flexible collapsible receptacle, and wherein the apparatus further comprises a pump configured intermediate the breath input interface and the container to impel the breath into the at least partially flexible collapsible receptacle at the volume increase rate.

19. The apparatus of claim 1, wherein the controller deactivates the pump when a change rate in the humidity level measured by the hygrometer is within a change rate target range.

20. The apparatus of claim 1, wherein the controller deactivates the pump when the humidity level measured by the hygrometer is within a range of 0% to an ambient air humidity level.

21. The apparatus of claim 20, wherein the controller deactivates the pump when the humidity level measured by the hygrometer is within a target range.

* * * * *